United States Patent
Alshaer et al.

(10) Patent No.: US 9,649,087 B2
(45) Date of Patent: May 16, 2017

(54) METHOD AND DEVICE FOR APNEA AND HYPOPNEA DETECTION

(75) Inventors: Hisham Alshaer, Mississauga (CA); Geoffrey Roy Fernie, Etobicoke (CA); T. Douglas Bradley, Toronto (CA)

(73) Assignee: UNIVERSITY HEALTH NETWORK, Toronto, Ontario (CA)

( * ) Notice: Subject to any disclaimer, the term of this patent is extended or adjusted under 35 U.S.C. 154(b) by 519 days.

(21) Appl. No.: 14/117,922

(22) PCT Filed: May 17, 2012

(86) PCT No.: PCT/CA2012/000478
§ 371 (c)(1),
(2), (4) Date: Feb. 24, 2014

(87) PCT Pub. No.: WO2012/155251
PCT Pub. Date: Nov. 22, 2012

(65) Prior Publication Data
US 2014/0194780 A1   Jul. 10, 2014

Related U.S. Application Data

(63) Continuation-in-part of application No. PCT/CA2011/000555, filed on May 17, 2011.
(Continued)

(51) Int. Cl.
*A61B 5/00* (2006.01)
*A61B 7/04* (2006.01)
(Continued)

(52) U.S. Cl.
CPC .............. *A61B 7/04* (2013.01); *A61B 5/4818* (2013.01); *A61B 5/6803* (2013.01);
(Continued)

(58) Field of Classification Search
CPC ................................................... A61B 5/4818
See application file for complete search history.

(56) References Cited

U.S. PATENT DOCUMENTS

| | | | |
|---|---|---|---|
| 4,648,407 A | 3/1987 | Sackner | |
| 5,671,733 A | 9/1997 | Raviv et al. | |

(Continued)

FOREIGN PATENT DOCUMENTS

| | | |
|---|---|---|
| CA | 2585824 | 9/2008 |
| EP | 2653108 | 10/2013 |

(Continued)

OTHER PUBLICATIONS

Nakano, Hiroshi, et al. "Validation of a new system of tracheal sound analysis for the diagnosis of sleep apnea-hypopnea syndrome." Sleep—New York Then Westchester-27.5 (2004): 951-958.*

(Continued)

*Primary Examiner* — Michael C Stout
*Assistant Examiner* — Nicholas E Kolderman
(74) *Attorney, Agent, or Firm* — Middleton Reutinger

(57) ABSTRACT

Disclosed herein is a method and device for apnea and hypopnea detection. In one embodiment, a method is provided for detecting apneas and hypopneas from a digitized breath sound recording acquired from a candidate suspected of sleep apnea. The method comprises scanning an amplitude profile of the digitized breath sound recording to identify a prospect event segment; evaluating characteristics of the prospect event segment for consistency with one or more preset apnea-specific criteria; classifying the prospect event segment as representative of an apnea upon it satisfying each of the one or more apnea-specific criteria; evaluating the prospect event characteristics for consistency with one or more preset hypopnea-specific criteria distinct from (Continued)

the apnea-specific criteria; and classifying the prospect event segment as representative of a hypopnea upon it satisfying each of the one or more hypopnea-specific criteria.

22 Claims, 18 Drawing Sheets

Related U.S. Application Data

(60) Provisional application No. 61/486,855, filed on May 17, 2011.

(51) Int. Cl.
 *A61B 7/00* (2006.01)
 *A61B 5/087* (2006.01)
(52) U.S. Cl.
 CPC ............ *A61B 5/7282* (2013.01); *A61B 7/003* (2013.01); *A61B 5/087* (2013.01); *A61B 5/7257* (2013.01); *A61B 2562/0204* (2013.01)

(56) References Cited

U.S. PATENT DOCUMENTS

| | | | |
|---|---|---|---|
| 5,782,240 | A | 7/1998 | Raviv et al. |
| 5,797,852 | A | 8/1998 | Karakasoglu et al. |
| 5,845,636 | A | 12/1998 | Gruenke et al. |
| 5,961,447 | A | 10/1999 | Raviv et al. |
| 6,045,514 | A | 4/2000 | Raviv et al. |
| 6,142,950 | A | 11/2000 | Allen et al. |
| 6,171,258 | B1 | 1/2001 | Karakasoglu et al. |
| 6,213,955 | B1 | 4/2001 | Karakasoglu et al. |
| 6,290,654 | B1 | 9/2001 | Karakasoglu |
| 6,368,287 | B1 | 4/2002 | Hadas |
| 6,375,623 | B1 | 4/2002 | Gavriely |
| 7,118,536 | B2 | 10/2006 | Haberland et al. |
| 7,225,021 | B1 | 5/2007 | Park et al. |
| 7,387,124 | B2 | 6/2008 | Noda et al. |
| 7,785,265 | B2 | 8/2010 | Schätzl |
| 7,850,619 | B2 | 12/2010 | Gavish et al. |
| 2002/0123699 | A1 | 9/2002 | Lambert et al. |
| 2005/0222502 | A1 | 10/2005 | Cooper |
| 2006/0196510 | A1 | 9/2006 | McDonald et al. |
| 2006/0266356 | A1 | 11/2006 | Sotos et al. |
| 2008/0001735 | A1 | 1/2008 | Tran |
| 2008/0243017 | A1 | 10/2008 | Moussavi et al. |
| 2008/0308105 | A1 | 12/2008 | Alder et al. |
| 2008/0319333 | A1 | 12/2008 | Gavish et al. |
| 2009/0118631 | A1* | 5/2009 | Gavish .................. A61B 7/003 600/529 |
| 2009/0293880 | A1 | 12/2009 | Rutan |
| 2010/0240982 | A1* | 9/2010 | Westbrook ............. A61B 5/087 600/391 |
| 2011/0105915 | A1 | 5/2011 | Bauer |

FOREIGN PATENT DOCUMENTS

| | | |
|---|---|---|
| GB | 2214302 | 8/1989 |
| WO | 0019895 | 4/2000 |
| WO | WO 01/15602 | 3/2001 |
| WO | WO 01/93743 | 12/2001 |
| WO | WO 2006/008745 | 1/2006 |
| WO | WO 2010/054481 | 5/2010 |
| WO | WO 2011/010384 | 1/2011 |
| WO | WO 2012/058727 | 5/2012 |

OTHER PUBLICATIONS

EP Extended Search Report for EP Application No. EP 12784876.0 (University Health Network) Apr. 17, 2015.
Nakano, Hiroshi, et al. "Validation of a new system of tracheal sound analysis for the diagnosis of sleep apnea-hypopnea syndrome." Sleep—New York Then Westchester—vol. 27 No. 5 (2004): 951-957. Aug. 1, 2004.
EP Extended Search Report for EP Application No. EP 12786596.2 (University Health Network) Mar. 20, 2015.
Abeyratne et al., "Pitch jump probability measures for the analysis of snoring sounds in apnea," *Physiological Measurement*, vol. 26, pp. 779-798, 2005.
Alshaer et al., "Adaptive segmentation and normalization of breathing acoustic data of subjects with obstructive sleep apnea," Paper presented at: *Science and Technology for Humanity (TIC-STH), 2009, IEEE Toronto International Conference*; Sep. 26-27, 2009.
Alshaer et al., "Development and validationof an algorithm for detection of apneas and hyponeas using overnight breath sound recordings," *American J. of Resp. Crit. Care Med.*, vol. 183, Meeting Abstracts A6317, D108 Diagnosis and Management of Sleep Disorders, Poster Discussion Session URL: http://aireem.atsjournals.org/cgi/reprint/183/1_meetingabstracts/A6317, (2011).
Alshaer et al., "Phase Tracking of the Breathing Cycle in Sleeping Subjects by Frequency Analysis of Acoustic Data," *International Journal of Healthcare Technology and Management*, vol. 11:3, pp. 163-175 (2010).
Argod, et al., "Differentiating Obstructive and Central Sleep Respiratory Events through Pulse Transit Time," *Am. J. Respir. Crit. Care Med.*, vol. 158:6, pp. 1778-1783 (1998).
Arzt et al., "Association of sleep-disordered breathing and the occurrence of stroke," *Am J Respir Crit Care Med*, vol. 172, pp. 1447-1451 (2005).
Bieger-Farhan et al., "Portable method for the determination of snoring site by sound analysis," Journal of Laryngology & Otology, vol. 118, pp. 135-138 (2004).
Bradley et al., "Sleep apnea and heart failure: Part I: obstructive sleep apnea," Circulation, vol. 107, pp. 1671-1678, Apr. 1, 2003.
Campbell et al., "The perception of wakefulness within sleep," *Sleep*, vol. 4, pp. 177-183 (1981).
Cavusoglu et al., "Investigation of sequential properties of snoring episodes for obstructive sleep apnoea identification," *Physiol Meas.*, vol. 29:8, pp. 879-898 (2008).
Dalmay et al., "Acoustic Properties of the Normal Chest," *Eur. Resp. Jrnl.*, vol. 8, pp. 1761-1769 (1995).
Duckitt et al., "Automatic detection, segmentation and assessment of snoring from ambient acoustic data," *Physiological Measurement*, vol. 27, pp. 1047-1056 (2006).
Fiz et al., "Analysis of forced wheezes in asthma patients," *Respiration*, vol. 73, pp. 55-60, (2006).
Fiz et al., "Detection of wheezing during maximal forced exhalation in patients with obstructed airways," *Chest*, vol. 122, pp. 186-191 (2002).
Fiz et al., "Acoustic analysis of snoring sound in patients with simple snoring and obstructive sleep apnea," *European Respiratory Journal*, vol. 9, pp. 2365-2370 (1996).
Fiz et al., Wheezing identification in asthma subjects during forced exhalation, *American Journal of Respiratory and Critical Care Medicine*, vol. 159, p. A652 (1999).
Folke et al., "Critical review of non-invasive respiratory monitoring in medical care," *Med Biol Eng Comput*, vol. 41, pp. 377-383 (2003).
Fritsch et al., "Monotone piecewise cubic interpolation," *SIAM Journal on Numerical Analysis*, vol. 17, pp. 238-246 (1980).
Gavriely et al., "Parametric representation of normal breath sounds," *J Appl Physiol*, vol. 73:5, pp. 1776-1784 (1992).
Guler et al., "Two-stage classification of respiratory sound patterns," *Comput Biol Med*, vol. 35, pp. 67-83 (2005).
Harrington et al., *Techniques in Speech Acoustics: Kluwer Academic Publisher* (1999).
Hill et al., "Palatal snoring identified by acoustic crest factor analysis," *Physiological Measurement*, vol. 20, pp. 167-174 (1999).
Hoffstein et al., "Snoring: is it in the ear of the beholder?" *Sleep*, vol. 17, pp. 522-526 (1994).
Hult et al., "A bioacoustic method for timing of the different phases of the breathing cycle and monitoring of breathing frequency," *Med Eng Phys*, vol. 22, pp. 425-433 (2000).
Hult et al., "An improved bioacoustic method for monitoring of respiration," *Technol Health Care*, vol. 12, pp. 323-332 (2004).

(56) References Cited

OTHER PUBLICATIONS

Jane et al., "Analysis of wheezes in asthmatic patients during spontaneous respiration," *Conf Proc IEEE Eng Med Biol Soc*, vol. 5, p. 3836 (2004).

Jane et al., "Automatic detection of snoring signals: Validation with simple snorers and OSAS patients," *Proceed of the 22nd Annual EMBS Int'l Conf.*, pp. 3129-3130 (2000).

Jane et al., "Automatic snoring signal analysis in sleep studies," *Proceed of the 25th Annual Int'l Conf of the IEEE EMBS*, Cancun, Mexico, pp. 366-369 (2003).

Leung et al., "Sleep apnea and cardiovascular disease," *Am J Respir Crit Care Med*, vol. 164, pp. 2147-2165 (2001).

MacKay, "Information Theory, Inference & Learning Algorithms," Cambridge, UK: *Cambridge University Press*, ch. 20, pp. 284-286 (2003).

Mattei et al., "Diagnosis of sleep apnea," *Minerva Med*, vol. 95, pp. 213-231 (2004).

Michael et al., "Analysed snoring sounds correlate to obstructive sleep disordered breathing," *European Archives of Oto-Rhino-Laryngology*, vol. 265:1, pp. 105-113 (2008).

Nakano et al., "Automatic detection of sleep-disordered breathing fro a single-channel airflow record," *European Respiratory Journal*, 29(4): 728-736 (2007).

Ng et al., "Could formant frequencies of snore signals be an alternative means for the diagnosis of obstructive sleep apnea?" *Sleep Medicine*, vol. 9:8, pp. 894-898 (2008).

Ng et al., "Role of upper airway dimensions in snore production: Acoustical and perceptual findings," *Annals of Biomedical Engineering.*, vol. 37:9, pp. 1807-1817 (2009).

Nieto et al., "Association of sleep-disordered breathing, sleep apnea, and hypertension in a large community-based study. Sleep Heart Health Study," *Jama*, vol. 283, pp. 1829-1836 (2000).

Perez-Padilla et al., "Characteristics of the snoring noise in patients with and without occlusive sleep apnea," *American Review of Respiratory Disease*, vol. 147:3, pp. 635-644 (1993).

Quinn et al., "The differentiation of snoring mechanisms using sound analysis," *Clinical Otolaryngology & Allied Sciences*, vol. 21, pp. 119-123 (1996).

Rabiner et al., "Fundamentals of Speech Recognition," *Prentice Hall*, p. 100-103 (1993).

Radfar et al., "A maximum likelihood estimation of vocal-tract-related filter characteristics for single channel speech separation," *EURASIP Journal on Audio, Speech, and Music Processing*, vol. 2007, Art. ID 84186, pp. 1-15 (2007).

Rechtschaffen et al., "A Manual of Standardized Terminology, Techniques and Scoring System for Sleep Stages of Human Subjects," *Los Angeles: UCLA Brain Information Service/Brain Research Institute* (1968).

Sankur et al., "Comparison of AR-based algorithms for respiratory sounds classification," *Comput Biol Med*, vol. 24, pp. 67-76 (1994).

Sankur et al., "Multiresolution biological transient extraction applied to respiratory crackles," *Comput Biol Med*, vol. 26, pp. 25-39 (1996).

Sen et al., "A multi-channel device for respiratory sound data acquisition and transient detection," *Conf Proc IEEE Eng Med Biol Soc*, vol. 6, pp. 6658-6661 (2005).

Shahar et al., "Sleep-disordered breathing and cardiovascular disease: cross-sectional results of the Sleep Heart Health Study," *Am J Respir Crit Care Med*, vol. 163, pp. 19-25 (2001).

Shiota et al., "Alterations in upper airway cross-sectional area in response to lower body positive pressure in healthy subjects," *Thorax*, vol. 62, No. 10, pp. 868-872, Oct. 2007.

"Sleep-related breathing disorders in adults: recommendations for syndrome definition and measurement techniques in clinical research," The Report of an American Academy of Sleep Medicine Task Force, *Sleep*. 1999, 22(5):667-689.

Sola-Soler et al., "Pitch analysis in snoring signals from simple snorers and patients with obstructive sleep apnea in Engineering in Medicine and Biology," *24th Annual Conf and the Annual Fall Mtg of the Biomedi Engineer Soc, EMBS/BMES Conf. Proceedings of the Second Joint* (2002).

Sola-Soler et al., "Variability of snore parameters in time and frequency domains in snoring subjects with and without Obstructive Sleep Apnea," *Conf Proc IEEE Eng Med Biol Soc*, vol. 3, pp. 2583-2586 (2005).

Steltner et al., "Diagnosis of Sleep Apnea by Automatic Analysis of Nasal Pressure and Forced Oscillation Impedance," *Am. J. Respir. Crit. Care Med.*, vol. 165:7, pp. 940-944 (2002).

Stock et al., "Development and application of a real-time monitoring and feedback system for deep inspiration breath hold based on external marker tracking," *Medical physics.*, vol. 33:8, p. 2868 (2006).

Thomas et al., "Differentiating Obstructive from Central and Complex Sleep Apnea Using an Automated Electrocardiogram-Based Method," *Sleep*, vol. 30:12, pp. 1756-1769 (2007).

Varady et al., "A novel method for the detection of apnea and hypopnea events in respiration signals," *IEEE Transactions on Biomedical Engineering*, 49(9): 936-942 (2002).

Vegfors et al., "Presentation and evaluation of a new optical sensor for respiratory rate monitoring," *Int J Clin Monit Comput*, vol. 11, pp. 151-156 (1994).

Wakwella et al., "Automatic Segmentation and Pitch/Jitter Tracking of Sleep Disturbed Breathing Sounds," *8th International Conf on Control, Automation, Robotics and Vision*, Kunming, China., IEEE, p. 936-940 (2004).

Wang et al., "A simple respiration gating technique and its application in high-resolution PET camera," *IEEE Transactions on Nuclear Science*, vol. 52:1, p. 125 (2005).

Werthammer et al., "Apnea monitoring by acoustic detection of airflow," *Pediatrics*, 71(1): 53-55 (1983).

Xiong et al., "Problems in Timing of Respiration with the Nasal Thermistor Technique," *J Am Soc of Echocardio*, vol. 6:2, pp. 210-216 (1993).

Yeginer et al., "Modeling of pulmonary crackles using wavelet networks," *Conf Proc IEEE Eng Med Biol Soc*, vol. 7, pp. 7560-7563 (2005).

Young et al., "The occurrence of sleep-disordered breathing among middle-aged adults," *N Engl J Med*, vol. 328, pp. 1230-1235 (1993).

Young et al., "Estimation of the clinically diagnosed proportion of sleep apnea syndrome in middle-aged men and women," *Sleep*, vol. 20, pp. 705-706 (1997).

International Preliminary Report on Patentability issued in Int'l Patent Application No. PCT/CA2009/001644 (2010).

International Search Report issued in Int'l Patent Application No. PCT/CA2011/000555 (2011).

International Search Report issued in Int'l Application No. PCT/CA2012/000494 (2012).

International Search Report issued in Int'l Application No. PCT/CA2012/000478 (2012).

\* cited by examiner

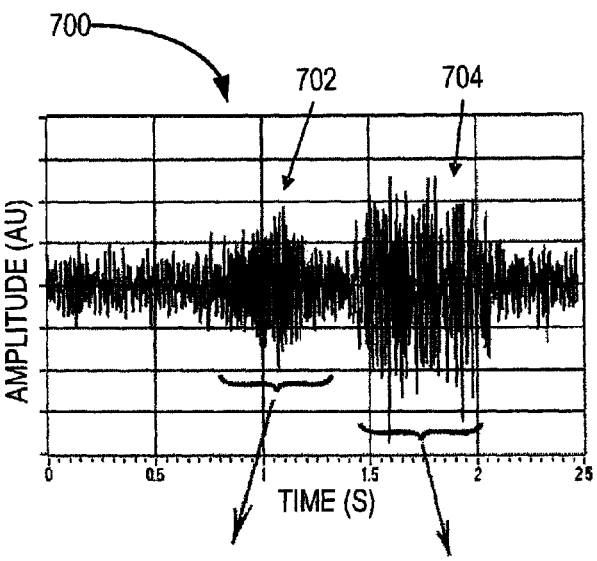
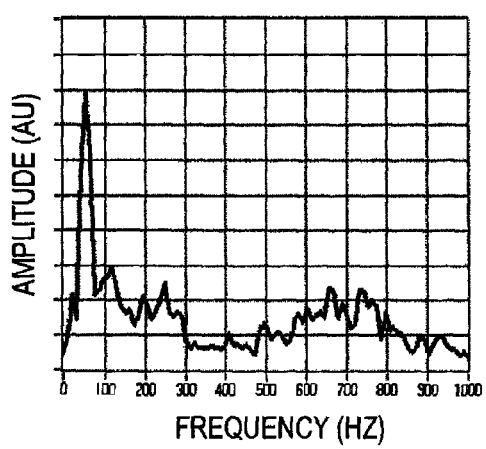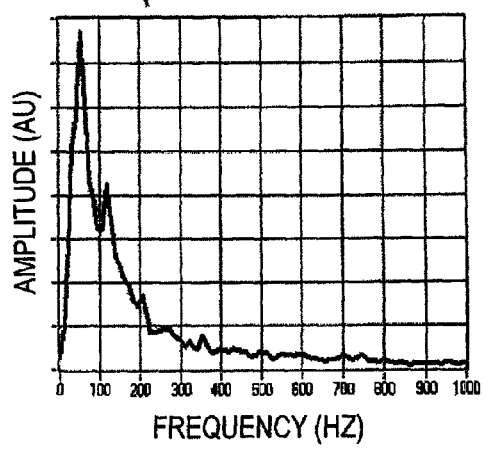
FIGURE 7A
FIGURE 7B
FIGURE 7C

METHOD AND DEVICE FOR APNEA AND HYPOPNEA DETECTION

CROSS REFERENCE TO RELATED APPLICATIONS

This patent application is a U.S. nationalization under 35 U.S.C. §371 of International Application No. PCT/CA2012/000478, filed May 17, 2012, which is a Continuation-in-Part of International Application No. PCT/CA2011/000555, filed May 17, 2011, and which claims the benefit of priority under 35 U.S.C. §119(e) to U.S. Provisional Application No. 61/486,855, filed May 17, 2011. The disclosures set forth in the referenced applications are incorporated herein by reference in their entireties.

FIELD OF THE DISCLOSURE

The present disclosure relates to the detection of breathing disorders, and in particular, to a method and device for apnea and hypopnea detection.

BACKGROUND

Sleep apnea (SA) is a breathing disorder characterized by repetitive complete or partial cessations of breathing (apneas and hypopneas, respectively) during sleep. The frequency of these events ranges from 5 to 100 times/hour depending on the severity of the case. As a result, patients suffer from poor sleep quality, daytime sleepiness, and poor cognitive performance. Sleep apnea can generally be characterized as one of two types—obstructive and central sleep apnea (OSA and CSA, respectively). It has been observed that OSA, which is the most common type, increases the risk of developing hypertension, heart failure (HF), and stroke by 3 to 4 fold. Also, patients with untreated sleep apnea generally consume twice as many healthcare resources for treatment of cardiorespiratory diseases than subjects without the disease. On the other hand, it has been demonstrated that treating OSA in patients with hypertension or HF lowers blood pressure, and dramatically improves cardiovascular function. Therefore, diagnosing and treating such patients could have a very substantial beneficial medical and public health impact. Unfortunately, the majority of people with sleep apnea remain undiagnosed due to the lack of accessibility to expensive overnight monitoring in a sleep laboratory presently required for diagnosis. Therefore, there is an increasing demand for developing reliable yet simple tools for diagnosing sleep apnea that can be accessed by a wider base of the population.

Obstructive sleep apnea (OSA) is generally understood to result from partial or complete collapse of the pharynx or the upper airway (UA) resulting in obstruction of the airflow pathway. In OSA, the respiratory drive is still present but the patient is breathing against a high resistance tube—a situation that mimics chocking. Thus, the hallmark of OSA is narrowing, obstruction, or total closure of the upper airway (pharynx). This results in characteristic breath sounds such as the occurrence of snoring and turbulent sounds. Each event generally lasts 10 to 60 seconds, thus generally causing episodes of oxygen deprivation and often provoking arousals from sleep and consequent sleep fragmentation. As a result, patients suffer from poor sleep quality, daytime sleepiness, and impaired cognitive performance. It is a common disease affecting approximately 7% of adults. Nevertheless, the majority of patients with OSA remain undiagnosed; in one study, it was shown that 93% of women and 82% of men with moderate to severe OSA had not been diagnosed.

Central sleep apnea (CSA), on the other hand, is generally understood to occur when there is a temporary cessation of respiratory output from the respiratory neurons in the brainstem to the muscles of respiration. This lack of respiratory muscle activation causes a temporary cessation of airflow (i.e. central apnea), during which there is no respiratory ventilation. In contrast to OSA, the upper airway is usually open during CSA, and thus chocking sounds and snoring are less likely to occur. When airflow resumes, snoring does not necessarily occur because the pharynx is usually not obstructed.

Presently, the standard means of identifying and diagnosing sleep apnea is via overnight polysomnography (PSG), in which the patients have to sleep in a laboratory attached to many monitoring electrodes under the supervision of a technician. PSG is expensive and access to it is limited, resulting in long waiting lists in the limited areas where PSG is available.

For this reason, interest has been raised in devising new methods to diagnose sleeping disorders, such as SA. For example, acoustic analysis of respiratory sounds has gained an increasing role in the study of respiratory disorders such as in identifying pathological respiratory sounds including wheezes and crackles, and to study and locate the site of snoring. In some sleep studies, snoring sounds were captured above the mouth level, as were tracheal sounds, to study snoring, particularly as snoring is a component of the disease itself and is produced at the very location where narrowing and obstruction takes place.

Despite recent findings, snore-driven techniques have fundamental limitations from the clinical perspective. For instance, snoring does not necessarily occur in all types of SA, such as in CSA. Furthermore, snore-driven techniques generally fail to assess the severity of an identified condition. For example, while snoring is a hallmark of OSA, it might not necessarily take place with each apnea and hypopnea. Accordingly, assessing the disease severity in terms of frequency of apneas per hour might be underestimated if some apneas are missed due to absence of snoring, for example. As knowledge about the disease severity can be beneficial in selecting an appropriate treatment strategy, snore-driven techniques can be less than ideal.

Accordingly, while some work has been done to detect the occurrence of OSA from snoring sounds, there remains much room for improvement, be it in the development of a reliable technique for detecting the occurrence of different types of SA and/or in providing a reliable approach for evaluating the severity of such occurrences, for example. Demand is also increasing for reliable apnea identification, characterization and/or diagnostic techniques that can be accessed by a wider base of the population, for example as compared to the technician-assisted PSG techniques currently implemented in dedicated sleep laboratories.

Therefore, there remains a need for a method and device for apnea and hypopnea detection that overcomes at least some of the drawbacks of known techniques, or at least, provides the public with a useful alternative.

This background information is provided to reveal information believed by the applicant to be of possible relevance to the invention. No admission is necessarily intended, nor should be construed, that any of the preceding information constitutes prior art against the invention.

SUMMARY

An object of the invention is to provide a method and device for apnea and hypopnea detection. In accordance with one embodiment of the invention, there is provided method for detecting apneas and hypopneas from a digitized breath sound recording acquired from a candidate suspected of sleep apnea, the method comprising: scanning an amplitude profile of said digitized breath sound recording to identify a prospect event segment; evaluating characteristics of said prospect event segment for consistency with one or more preset apnea-specific criteria; classifying said prospect event segment as representative of an apnea upon it satisfying each of said one or more apnea-specific criteria; evaluating said prospect event characteristics for consistency with one or more preset hypopnea-specific criteria distinct from said apnea-specific criteria; and classifying said prospect event segment as representative of a hypopnea upon it satisfying each of said one or more hypopnea-specific criteria.

In accordance with one such embodiment, the method is automatically implemented by one or more processors of a computing system, and further comprises outputting, via a user interface, an indication of a candidate's condition as a function of each classified apnea and hypopnea.

In accordance with another embodiment, there is provided a computer-readable medium comprising statements and instructions stored thereon for implementation by one or more processors of a computing system to detect apneas and hypopneas from a digitized breath sound recording acquired from a candidate suspected of sleep apnea, in accordance with the steps of the above method.

In accordance with another embodiment of the invention, there is provided a system for detecting apneas and hypopneas from a digitized breath sound recording acquired from a candidate suspected of sleep apnea, the system comprising: one or more processors; a computer-readable medium accessible by said one or more processors and having stored thereon statements and instructions executable thereby to operate on said recording in accordance with the above method.

In accordance with one such embodiment, the system further comprises a face mask having a microphone mounted thereon and reproducibly disposable, upon the candidate wearing the mask, at a distance above a nose and mouth area of the candidate so to intercept and capture expiratory airflow sounds emanating therefrom to be digitized for processing.

In accordance with another embodiment of the invention, there is provided a method for identifying a hypopnea from a digitized breath sound recording acquired from a candidate suspected of sleep apnea, the method comprising: identifying a low amplitude segment in a breath amplitude profile of the recording; calculating a decreasing profile amplitude gradient leading to said low amplitude segment; and classifying said low amplitude segment as a hypopnea only upon said decreasing profile amplitude gradient exceeding a preset minimum gradient.

In accordance with one such embodiment, the method is automatically implemented by one or more processors of a computing system, and further comprises outputting, via a user interface, an indication of each said classified hypopnea.

In accordance with another embodiment, there is provided a method for automatically determining a sleep apnea severity index from a digitized breath sound recording acquired from a candidate suspected of sleep apnea, the method comprising: scanning an amplitude profile of said digitized breath sound recording to identify a prospect event segment; evaluating characteristics of said prospect event segment for consistency with at least one of: one or more preset apnea-specific criteria, and one or more preset hypopnea-specific criteria distinct from said apnea-specific criteria; increasing an apneic event count upon said prospect event segment satisfying each of said one or more apnea-specific criteria or each of said one or more hypopnea-specific criteria; repeating said steps for multiple prospect event segments; and determining the sleep apnea severity index as a function of a total apneic event count.

In accordance with another embodiment, there is provide a system for automatically determining a sleep apnea severity index from a digitized breath sound recording acquired from a candidate suspected of sleep apnea, the system comprising: one or more processors; and a computer-readable medium accessible by said one or more processors and having stored thereon statements and instructions executable thereby to operate on said recording in accordance with the above method.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 7A is an illustrative waveform plot of breathing sounds acquired from a single breath showing both an inspiration phase and an expiration phase, whereas FIGS. 7B and 7C are exemplary FFT spectra for respective time segments of the inspiration phase and expiration phase of FIG. 7A, in accordance with one embodiment of the invention;

FIGS. 10A to 10C are plots of successively preprocessed digitized breathing sounds, wherein FIG. 10B is a plot of the digitized breathing sounds of FIG. 10A with outliers removed and a segment thereof defined for segment-based normalization, and wherein FIG. 10C is a plot of the digitized breathing sounds of FIG. 10B after segment-based normalization, in accordance with one embodiment of the invention;

DETAILED DESCRIPTION

With reference to the disclosure herein and the appended figures, a method and apparatus for apnea and hypopnea detection are described in accordance with different embodiments of the invention. For instance, and as will be discussed in greater detail below, the methods and devices described herein according to different embodiments of the invention, allow to automate at least some of the analyses/evaluations associated with the detection of breathing disorders such as apnea and hypopnea, using breath sound recordings. For example, recordings of an individual's breath-related sounds during sleep can be recorded and analyzed, using at least some of the methods described herein, to detect and identify distinct apneas and hypopneas for the purpose of diagnosing this individual's breathing disorder(s) and providing adequate treatment therefor.

In some embodiments, such methods and devices rely, at least in part, on the analysis of breath-related sounds. For example, in some embodiments, the methods and devices described herein can be used to detect sleep apnea via acoustic breath sound analysis, such as from overnight breath sound recordings and the like, and in some embodiments, to further quantify a severity of this disorder in a given subject, and/or achieve other related characterizations of the subject's condition. Such results present significant improvements in the provision of a less invasive approach to sleep apnea identification, characterization and/or diagnosis, particularly as compared to PSG and other, such techniques. Namely, and in accordance with some embodiments, useable results can be achieved using as few as a single non-invasive acoustic breathing sound channel to achieve sleep apnea identification, characterization and/or diagnosis, which may further include characterization of a severity of the identified apnea. In some embodiments such results may be achieved irrespective of the type of apnea experienced by the candidate (e.g. OSA and/or CSA).

Figure 1:
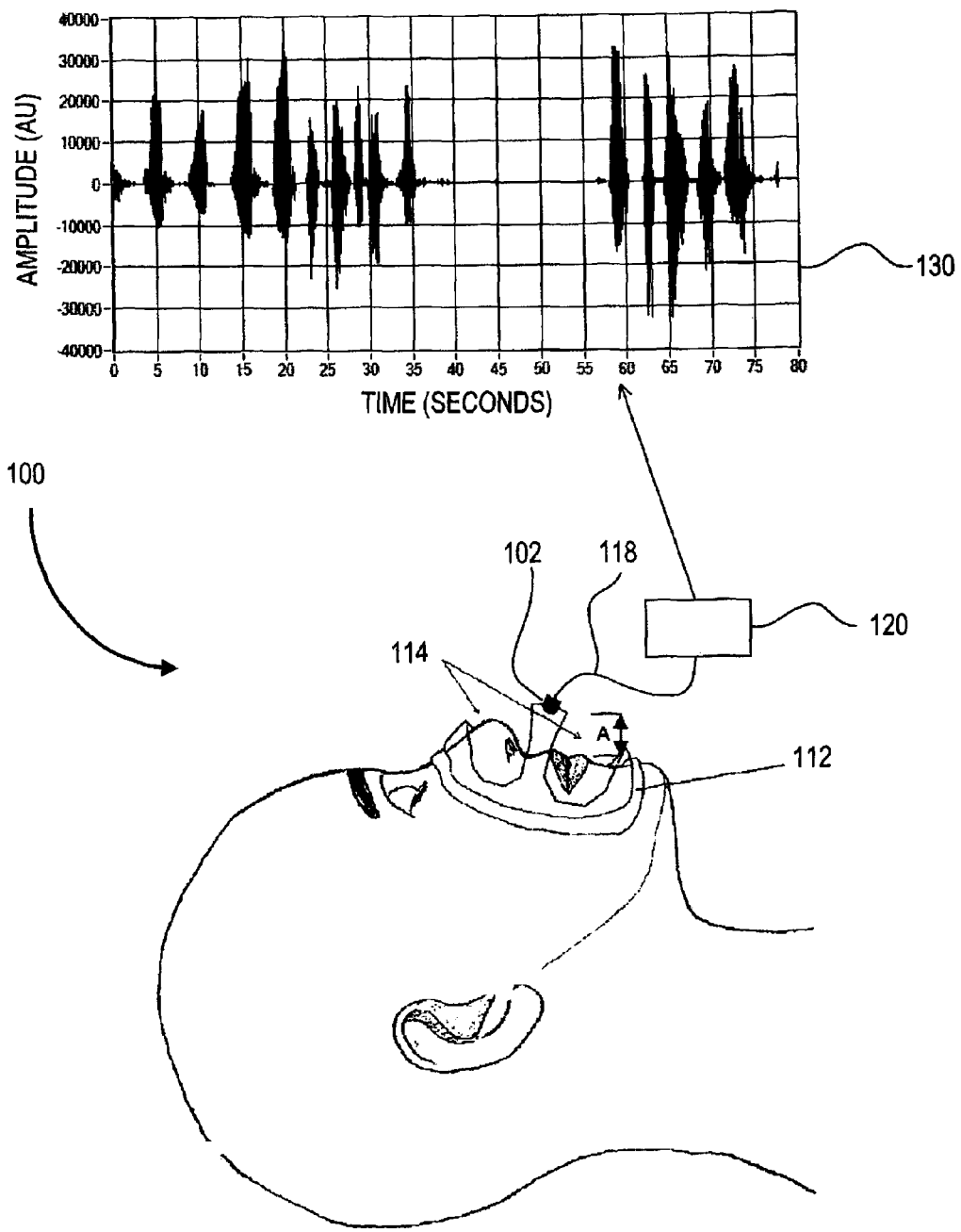
FIG. 1 is a diagram of an apnea and hypopnea detection system, in accordance with one embodiment of the invention.

With reference now to FIG. 1, a system for apnea and/or hypopnea detection, generally referred to using the numeral 100, and in accordance with an illustrative embodiment of the invention, will now be described. In this embodiment, the system 100 generally provides for the recordal of breath sound data, in this example, via one or more transducers, such as microphone 102, disposed at a distance A from a nose and mouth area of a candidate's face in a face mask 112 to be worn by the candidate during testing. For example, the mask may be worn during sleep if seeking to identify sleep-related disorders such as sleep apnea. As schematically depicted, the one or more transducers 102 are operatively coupled to a data recording/processing module 120 for recording breath sound data, illustratively depicted by raw signal plot 130, for processing.

In this example, the microphone 102 is coupled in or to a loose fitting full face mask 112 which includes at least one opening 114 to allow for ease of breathing, and provides for a communication path 118, be it wired and/or wireless, from the microphone 102 to the recording/processing module 120.

Figure 2:
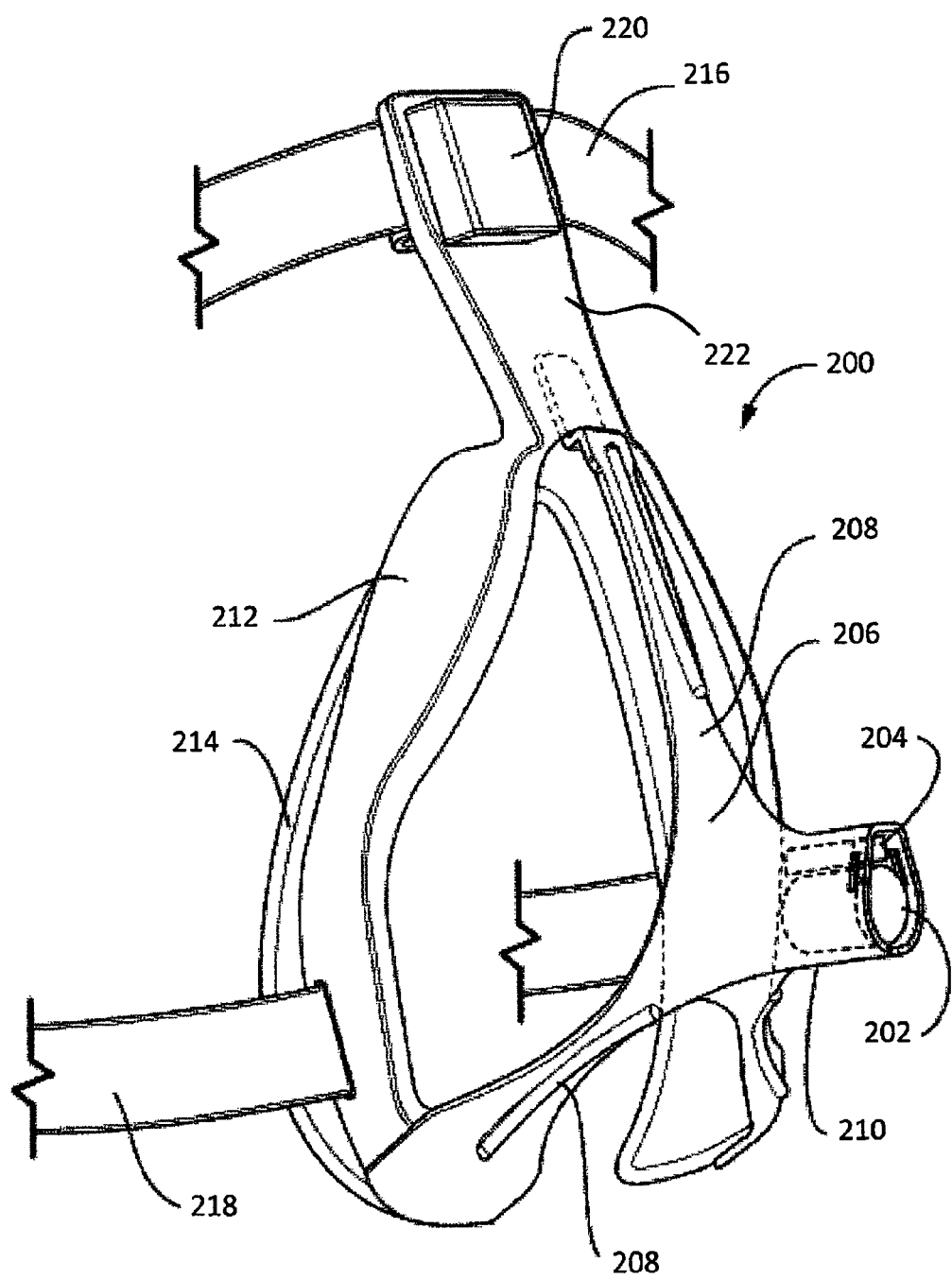
FIG. 2 is a perspective view of a mask for use in acquiring breathing sounds from a candidate, for example within the context of the system of FIG. 1, in accordance with one embodiment of the invention.

FIG. 2 provides another example of a mask 200 usable in acquiring breathing sounds suitable in the present context. In this example, the mask 200 generally comprises at least one transducer, such as microphones 202 and 204, and a support structure 206 for supporting same above a nose and mouth area of the subject's face. The support structure 206 is generally shaped and configured to rest on the subject's face and thereby delineate the nose and mouth area thereof, and comprises two or more outwardly projecting limbs 208 (e.g. three limbs in this example) that, upon positioning the mask 200, converge into a transducer supporting portion 210 for supporting microphones 202 and 204 at a distance from this area.

The support structure further comprises an optional frame 212 and face resting portion 214 shaped and configured to contour the face of the subject and at least partially circumscribe the nose and mouth area of the subject's face, thereby facilitating proper positioning of the mask on the subject's face and providing for greater comfort. A restraining mechanism, such as head straps 216 and 218, can be used to secure the mask to the subject's face and thereby increase the likelihood that the mask will remain in the proper position and alignment during use, e.g. even when the subject is sleeping in monitoring certain breathing disorders such as sleep apnea.

In this embodiment, the mask 200 further comprises an integrated recording device 220, such as a digital recording device or the like, configured for operative coupling to the at least one transducer, such as microphones 202 and 204, such that sound and/or airflow signals generated by the at least one transducer can be captured and stored for further processing, for example via one or more data processing modules (not shown). In this particular embodiment, the recording device 220 is disposed on a frontal member 222 of the support structure 206, thereby reducing an obtrusiveness thereof while remaining in close proximity to the at least one transducer so to facilitate signal transfer therefrom for recordal. In providing an integrated recording device, the mask 200 can effectively be used as a self-contained respiratory monitoring device, wherein data representative of the subject's breathing can be stored locally on the mask and transferred, when convenient, to a remotely located respiratory diagnostic center, for example. Further details as to the design, features and use of mask 200 are provided in U.S. Patent Application Publication No. 2011/0092839 and International Application Publication No. WO 2012/037641, the entire contents of each one of which is hereby incorporated herein by reference.

Figure 3:
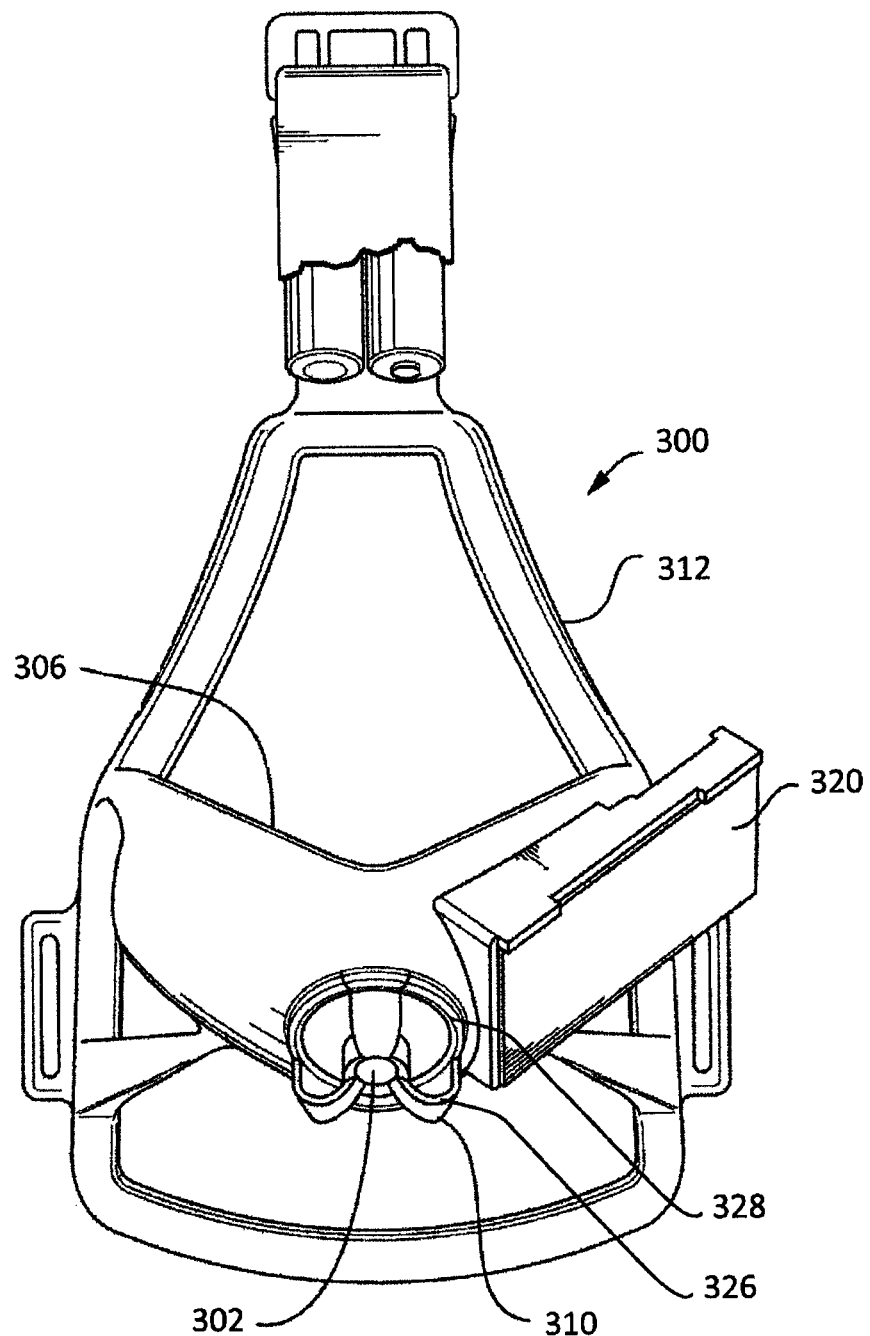
FIGS. 3 and 4 are front and side views, respectively, of a mask for use in acquiring breathing sounds from a candidate, for example within the context of the system of FIG. 1, in accordance with another embodiment of the invention.
Figure 4:
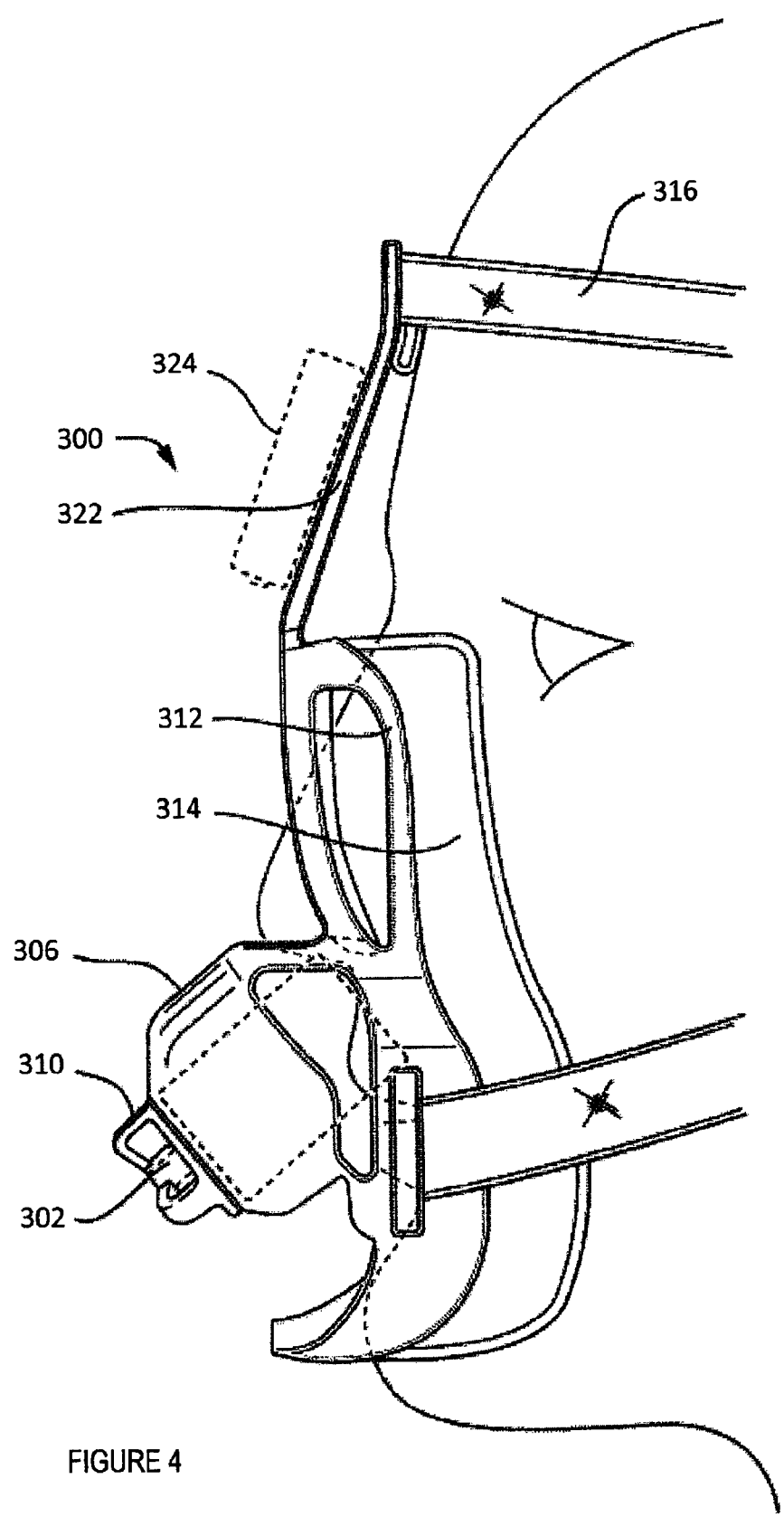

FIGS. 3 and 4 provide yet another example of a mask 300 usable in acquiring breathing sounds suitable in the present context. In this example, the mask 300 comprises at least one transducer, such as microphone 302, and a support structure 306 for supporting same above a nose and mouth area of the subject's face. The support structure 306 is generally shaped and configured to rest on the subject's face and extend outwardly therefrom over a nose and mouth area thereof to provide a transducer supporting portion 310 for supporting the microphone 302, upon positioning the mask, at a distance from this area.

In this example, the support structure 306 is shaped and configured to support the transducer 302 above the nose and mouth area at a preset orientation in relation thereto, wherein the preset orientation may comprise one or more of a preset position and a preset angle to intercept airflow produced by both the subject's nose and mouth. For example, in one embodiment, the preset orientation may be preset as a function of an estimated intersection between nasal and oral airflow, for example based on an observed or calculated average intersection between such airflows. For instance, in one embodiment, the preset orientation may comprise a preset position that, upon positioning the mask on the subject's face, is substantially laterally centered relative to the subject's face and longitudinally substantially in line with or below the subject's mouth, thus generally intercepting oral and nasal airflow.

In a same or alternative embodiment, the preset orientation may comprise a preset angle that aligns the microphone, or a principle responsiveness axis thereof, along a line more or less representative of an averaging between general oral and nasal airflows. For instance, in one embodiment, the orientation angle is preset to more or less bisect an angle formed by the transducer's preset position relative to the subject's nose (i.e. nostrils) and mouth. This bisecting angle, which should be construed within the present context to represent an angle more or less directing the transducer's principal responsiveness axis toward a point somewhere between the wearer's nose and mouth, may be determined as a function of measured, observed and/or otherwise estimated nasal and oral breathing patterns, so to improve or enhance the transducer's general responsiveness to airflow originating from the nose and/or mouth of the candidate. Generally, the preset orientation may thus, in accordance with one embodiment, of the invention, comprise a preset angle that, upon positioning the mask on the subject's face, substantially aligns the transducer with a point between the subject's nose and mouth.

In this embodiment, the support structure 306 generally comprises two outwardly projecting limbs that flow continuously one within the other toward the transducer supporting portion 310 in defining a funneling shape that substantially converges toward this transducer supporting portion, thus effectively redirecting nasal and/or oral airflow toward the transducer 302 and allowing for effective monitoring of airflow produced by both the subject's nose and mouth while breathing. Accordingly, breathing airflow, which will generally more or less diverge laterally from the candidate's nostrils as it is projected more or less obliquely downward therefrom, can be effectively collected, at least partially, by the generally concave support structure 306 to be substantially funneled thereby toward the transducer 302.

Accordingly, in this embodiment, not only is the transducer's preset orientation generally selected as a function of an estimated nasal and oral airflow intersection, the general funneling shape of the support structure 306 will further redirect at least a portion of laterally diverging nasal (and oral) airflow toward the transducer 302. Similarly, though not explicitly depicted herein, the same generally concave shape of the funneling support structure 306 will, partly due to its upwardly titled orientation in this embodiment, also at least partially redirect longitudinally divergent airflow toward the transducer 302.

The transducer supporting portion 310 of the support structure 306 further comprises one or more (three in this embodiment) transducer supporting bridges or limbs 326 extending from a transducer-surrounding aperture 328 defined within the support structure 306. In this embodiment, the provision of bridging limbs 326 may allow for a general reduction in airflow resistance, which may result in substantially reduced dead space. For example, while the general funneling shape of the support structure 306 allows for a redirection of airflow toward the transducer 302, the bridged aperture 328 allows for this flow of air to continue beyond the transducer 302, and thereby reduce the likelihood of this flowing air pooling within the mask and/or flowing back onto itself, which could otherwise lead to a generally uncomfortable warm/humid flow of breath back in the candidate's face (and which could thus be breathed in again), and/or lead to unusual flow patterns and/or sounds that could further complicate data processing techniques in accounting for these patterns.

The support structure 306 further comprises an optional frame 312 and face resting portion 314 shaped and configured to contour the face of the subject and at least partially circumscribe the nose and mouth area of the subject's face, thereby facilitating proper positioning of the mask on the subject's face and providing for greater comfort. A restraining mechanism, such as head straps 316, can be used to secure the mask to the subject's face and thereby increase the likelihood that the mask will remain in the proper position and alignment during use, even when the subject is sleeping, for example, in monitoring and diagnosing certain common breathing disorders. It will be appreciated that the data analysis techniques described below may also be applicable, in some conditions, in monitoring and diagnosing a subject's breathing when awake.

In this embodiment, the mask 300 further comprises a recording device 320, such as a digital recording device or the like, configured for operative coupling to the at least one transducer 302, such that breath sound signals generated by the at least one transducer can be captured and stored for further processing. In this particular embodiment, the recording device 320 is disposed on one of the limbs of the support structure 306, thereby reducing an obtrusiveness thereof while remaining in close proximity to the at least one transducer so to facilitate signal transfer therefrom for recordal. A battery pack 324, operatively coupled to the recording device 320, is provided on a frontal member 322 of the mask 300 to power the recording device and transducer in acquiring data free of any external wiring or the like. In providing an integrated and self-supported recording device, the mask 300 can effectively be used as a self-contained respiratory monitoring device, wherein data representative of the subject's breathing can be stored locally on the mask and transferred, when convenient, to a remotely located respiratory diagnostic center, for example.

Further details as to the design, features and use of mask 300 are provided in International Application Publication No. WO 2012/037641, the entire contents of which is incorporated herein by reference.

As will be appreciated by the person of ordinary skill in the art, the general shape and design of the above-described masks (200, 300) can provide, in different embodiments, for an improved responsiveness to airflow produced by the subject while breathing, and that irrespective of whether the subject is breathing through the nose or mouth, predominantly through one or the other, or through both substantially equally. Namely, the ready positioning of an appropriate transducer responsive to airflow relative to the nose and mouth area of the subject's face is provided for by the general spatial configuration of these masks. Accordingly, great improvements in data quality, reliability and reproducibility can be achieved, and that, generally without the assistance or presence of a health care provider, which is generally required with previously known systems.

Furthermore, it will be appreciated that different manufacturing techniques and materials may be considered in manufacturing the above and similar masks, for example as described below, without departing from the general scope and nature of the present disclosure. For example, the entire mask may be molded in a single material, or fashioned together from differently molded or otherwise fabricated parts. For example, the outwardly projecting nosepiece of the mask may comprise one part, to be assembled with the frame and face-resting portion of the mask. Alternatively, the frame and nosepiece may be manufactured of a single part, and fitted to the face-resting portion thereafter. As will be further appreciated, more or less parts may be included in different embodiments of these masks, while still providing similar results. For example, the nose piece, or an equivalent variant thereof, could be manufactured to rest directly on the subject's face, without the need for a substantial frame or face resting portions. Alternatively or in addition, different numbers of outwardly projecting limbs (e.g. two, three, four, etc.) or structures may be considered to provide similar results.

In general, the at least one transducer in the above examples, and their equivalents, is responsive to sound and/or airflow for generating a data signal representative of breathing sounds to be used in implementing different embodiments of the below-described methods. For example, in the illustrated embodiment of FIG. 2, two microphones 202 and 204 are provided in the transducer support portion 210, wherein one of these microphones may be predominantly responsive to sound, whereas the other may be predominantly responsive to airflow. For example, the microphone configured to be predominantly responsive to airflow may be more sensitive to air pressure variations then the other. In addition or alternatively, the microphone configured to be predominantly responsive to sound may be covered with a material that is not porous to air. In addition or alternatively, the microphone configured to be predominantly responsive to sound may be oriented away from the subject's nose and mouth so to reduce an air impact on the diaphragm of this microphone produced by the subject's breathing airflow. In other embodiments, a microphone predominantly responsive to airflow may be positioned in the transducer support portion in line with the subject's nose and mouth, while another microphone may be positioned to the side or on the periphery of the mask to thereby reduce an influence of airflow thereon. In some of these embodiments, the recorded sound from the peripheral microphone, or again from the microphone predominantly responsive to sound, may in fact be used to isolate the airflow signal recorded in the nosepiece, by filtering out the sound signal recorded thereby, for example.

In the embodiments of FIGS. 1, 3 and 4, however, a single microphone may alternatively be used to capture both sound and airflow, wherein each signal may be optionally distinguished and at least partially isolated via one or more signal processing techniques, for example, wherein a turbulent signal component (e.g. airflow on microphone diaphragm) could be removed from other acoustic signal components (e.g. snoring). Such techniques could include, but are not limited to adaptive filtering, harmonics to noise ratio, removing harmonics from a sound recording, wavelet filtering, etc.

In each of the above examples, the device may be implemented using a single type of transducer, for example one or more microphones which may in fact be identical. It will be appreciated however that other types of transducers, particularly responsive to airflow, may be considered herein without departing from the general scope and nature of the present disclosure. For example, a pressure sensor or airflow monitor may be used instead of a microphone to yield similar results in capturing an airflow produced by the subject while breathing.

It will be appreciated by the skilled artisan that different types of masks, or other means for recording breath sounds, may be considered herein without departing from the general scope and nature of the present disclosure. Namely, while the above examples provide for one means for acquiring breath sound data in implementing the below-described analysis methods, other means will be readily apparent to the person of ordinary skill in the art and should thus be considered to fall within the context of the present disclosure.

In the above examples, acquired breath sound data is generally communicated to data recording/processing module 120, 220, 320, which may comprise a single self-contained module, or a number of distinct and communicatively coupled or coupleable modules configured to provide complimentary resources in implementing the below-described methods. Namely, the recording/processing module may comprise a distinctly implemented device operatively coupled to one or more breath sound transducers for communication of data acquired thereby via, for example, one or more data communication media such as wires, cables, optical fibres, and the like, and/or one or more wireless data transfer protocols, as would be readily appreciated by one of ordinary skill in the art. A distinct recording module may, however, in accordance with another embodiment, be implemented integrally with the mask, and used to later communicate recorded data, be it raw and/or preprocessed data, to a remote or distinct processing device. As will be appreciated by the skilled artisan, the processing module may further be coupled to, or operated in conjunction with, an external processing and/or interfacing device, such as a local or remote computing device or platform provided for the further processing and/or display of raw and/or processed data, or again for the interactive display of system implementation data, protocols and/or diagnostics tools.

Figure 5:
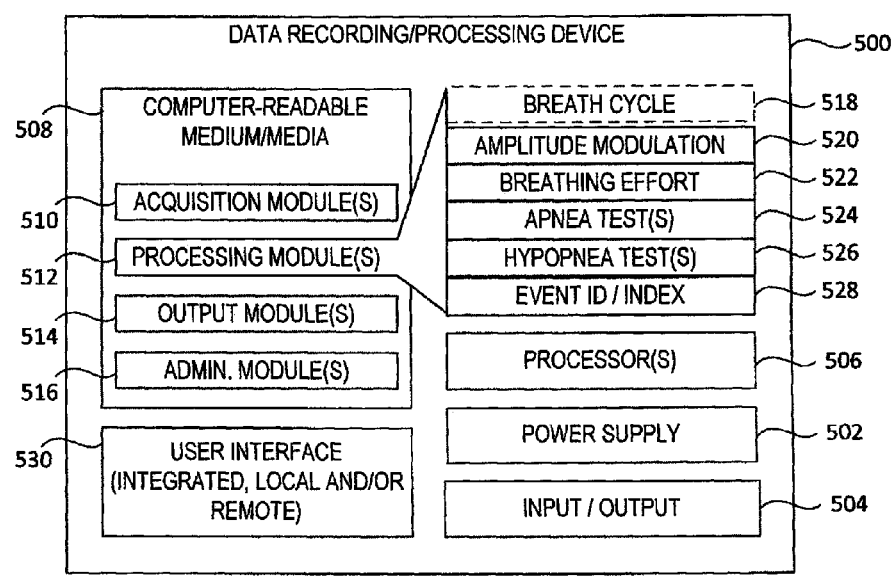
FIG. 5 is a schematic diagram of a breathing sound recording/processing device, for use for example within the context of the system of FIG. 1, in accordance with one embodiment of the invention.

With reference to FIG. 5, the processing module, depicted herein generically as a self-contained recording/processing device 500, generally comprises a power supply 502, such as a battery or other known power source, and various input/output port(s) 504 for the transfer of data, commands, instructions and the like with interactive and/or peripheral devices and/or components (not shown), such as for example, a breath monitoring mask or the like (as shown in FIGS. 1 to 4), external data processing module, display or the like.

The device 500 further comprises one or more computer-readable media 508 having stored thereon statements and instructions, for implementation by one or more processors 506, in automatically implementing various computational tasks with respect to, for example, breath sound data acquisition and processing. Such tasks may include, but are not limited to, the implementation of one or more breathing disorder identification, characterization and/or diagnostic tools implemented on or in conjunction with the device 500. In the illustrative example of FIG. 5, these statements and instructions are represented by various sub-modules and/or subroutines to be called upon by the processors 506 to operate the device in recording and processing breathing sounds in accordance with the various breath disorder identification, characterization and diagnostic methods discussed below. Illustratively, the processing platform will include one or more acquisition module(s) 510 for enabling the acquisition and digitization of breath sounds generated by the candidate while breathing; one or more processing module(s) 512 for processing the acquired data in identifying, characterizing and/or diagnosing a potential breathing disorder; one or more admin. module(s) 516 for receiving as input various processing parameters, thresholds and the like, which may be varied from time to time upon refinement and/or recalibration of the system or based on different user or candidate characteristics; and one or more output module(s) 514 configured to output process results in a useable form, either for further processing, or for immediate consumption (e.g. breath disorder identification, characterization and/or diagnosis results, indicia, and the like). For the purpose of illustration, the processing module(s) 512 in this particular example, and with reference to the high level and detailed processes of FIGS. 6 and 8, respectively, may include, but are not limited to, an optional breath cycle identification module 518 (e.g. to identify and isolate expiratory breathing phases), a breath sound amplitude modulation module 520, a breathing effort extraction module 522 (e.g. to identify prospective events based on observed breathing effort variations), apnea/hypopnea test modules 524/526, and an event identification module 528 (e.g. to generate an event identification, overall count and/or severity index such as a apnea-hypopnea index—AHI), to name a few examples. It will be appreciated that different embodiments may implement different subsets and combinations of the above modules to achieve different results depending on the intended purpose of the device and/or known or suspected candidate conditions. Furthermore, while not explicitly illustrated, one or more of the above-noted processing modules may be equally subdivided into one or more submodules consistent with preset processes to be implemented thereby, for example as described hereinbelow in accordance with different illustrative embodiments of the invention. Clearly, while the above contemplates the provision of a modular processing architecture, other process architectures may be readily applied to the present context, as will be appreciated by the person of ordinary skill in the art, without departing from the general scope and nature of the present disclosure.

The device 500 may further comprise a user interface 530, either integral thereto, or distinctly and/or remotely operated therefrom for the input of data and/or commands (e.g. keyboard, mouse, scroll pad, touch screen, push-buttons, switches, etc.) by an operator thereof, and/or for the presentation of raw, processed and/or diagnostic data with respect to apnea/hypopnea detection, monitoring and/or diagnostic (e.g. graphical user interface such as CRT, LCD, LED screen or the like, visual and/or audible signals/alerts/warnings/cues, numerical displays, etc.).

As will be appreciated by those of ordinary skill in the art, additional and/or alternative components operable in conjunction and/or in parallel with the above-described illustrative embodiment of device/module 500 may be considered herein without departing from the general scope and nature of the present disclosure. It will further be appreciated that device/module 500 may equally be implemented as a distinct and dedicated device, such as a dedicated home, clinical or bedside apnea/hypopnea detection device, or again implemented by a multi-purpose device, such as a multi-purpose clinical or bedside device, or again as an application operating on a conventional computing device, such as a laptop or PC, or other personal computing devices such as a PDA, smartphone, or the like.

Furthermore, it will be appreciated that while a single all-encompassing device 500 is schematically depicted herein, various functionalities and features of the device may rather be distributed over multiple devices operatively and/or communicatively coupled to achieve a similar result. For example, in one embodiment, at least part of the functionalities of device 500 will be implemented on a local processing device integral to a self-contained breath monitoring mask, such as depicted by the embodiments of FIGS. 2 to 4. In such embodiments, the power supply, such as batteries, may be integral to the mask as well, thus providing a self-contained unit to be worn by the candidate during sleep without interference from cumbersome wires or wire harnesses. In such embodiments, the integrated processing device may be operatively coupled to the mask's one or more transducers, e.g. via one or more internal wires or a wireless link, so to provide self-contained recordal of breathing sounds during use.

The integrated device may be configured to record the raw data for subsequent transfer and processing, or may be preconfigured to implement various preprocessing and/or processing steps locally. For example, the local processing device may preprocess the recorded data in real-time to facilitate subsequent transfer, such as by digitizing the data, applying certain filters and/or amplifiers, and the like. In such embodiments, breathing sound data may be transferred in real-time, for example where the integrated device is operatively coupled to a wireless transceiver or the like, or again transferred in batches, for example, at the end of each sleep session. In the latter case, the integrated device may provide a wired or pluggable communication port for coupling to a computing device, either for immediate processing thereby, or again for communication of the recorded data to a remote processing platform (e.g. operated by a diagnostic or medical center). Alternatively, the recorded data may be stored by the integrated device on a removable medium, to be transferred to an appropriate reader for download and processing.

In other embodiments, further processing may be implemented locally on the self-contained device, with appropriate output available so to provide the user immediate access to at least some of the processed results. For example, and as will be discussed in greater detail below, preliminary results may be rendered available to the user for immediate consumption, such as an indication as to the likelihood that the candidate suffers from sleep apnea, a preliminary indication as to the severity thereof, and/or a full diagnostic of the user's condition, to name a few.

Breathing disorders are traditionally monitored and diagnosed using data acquired at sleep centers, where subjects are fitted with a number of electrodes and other potentially invasive monitoring devices, and monitored while they sleep. Clearly, as the subject is both required to sleep in a foreign setting with a number of relatively invasive and obtrusive monitoring devices attached to them, the data collected can often be misleading, if the subject even ever manages to get any sleep to produce relevant data.

Furthermore, known respiratory diagnostic systems generally require the acquisition of multiple sensory data streams to produce workable results that may include breath sounds, airflow, chest movements, esophageal pressure, heart rate, etc. Similarly, known portable monitoring devices proposed for the diagnosis of sleep apnea generally require subjects to adequately position and attach several wired electrodes responsive to a number of different biological parameters, such as listed above, which generally reduces the comfort and compliance of subjects and increases chances of detachment and/or displacement of the electrodes. Given that portable sleep apnea monitors are used in the absence of an attending health care professional, inaccurate placement or displacement of electrodes cannot be easily detected until the data is transferred to the health center.

In comparison, the provision of a portable mask for use in recording breathing sounds useable in the above-described system and below-described methods may provide a number of advantages over known techniques, including, but not limited to, patient comfort, ease of use, processing from single source data, etc.

In one exemplary embodiment, the recorded data is stored, and optionally encrypted on a removable data storage device, such as an SD card or the like. For example, analog data acquired by the one or more transducers can be locally pre-amplified, converted into digital data and stored in the removable memory device. The stored data can then either be uploaded from the memory card to a local computing device (e.g. laptop, desktop, palmtop, smartphone, etc.) for transmittal to a remotely located diagnostic center via one or more wired and/or wireless communication networks, or physically shipped or delivered to the remotely located diagnostic center for processing.

It will be appreciated that different types of data transfer and communication techniques may be implemented within the present context without departing from the general scope and nature of the present disclosure. For example, while the above example contemplates the use of a digital recording device having a removable data storage medium, such as a memory card of the like, alternative techniques may also be considered. For example, the recording device may rather include a wireless communication interface wherein data integrally recorded thereon can be wirelessly uploaded to a computing device in close proximity thereto. For example, Wi-Fi or Bluetooth applications may be leveraged in transferring the data for downstream use. Alternatively, the device may include a communication port wherein recorded data may be selectively uploaded via a removable communication cable, such as a USB cable or the like. In yet another example, the recording device itself may be removably coupled to the mask and provided with a direct communication interface, such as a USB port or the like for direct coupling to an external computing device. These and other such examples are well within the realm of the present disclosure and therefore, should not, nor should their equivalents, be considered to extend beyond the scope of the present disclosure.

Figure 6:
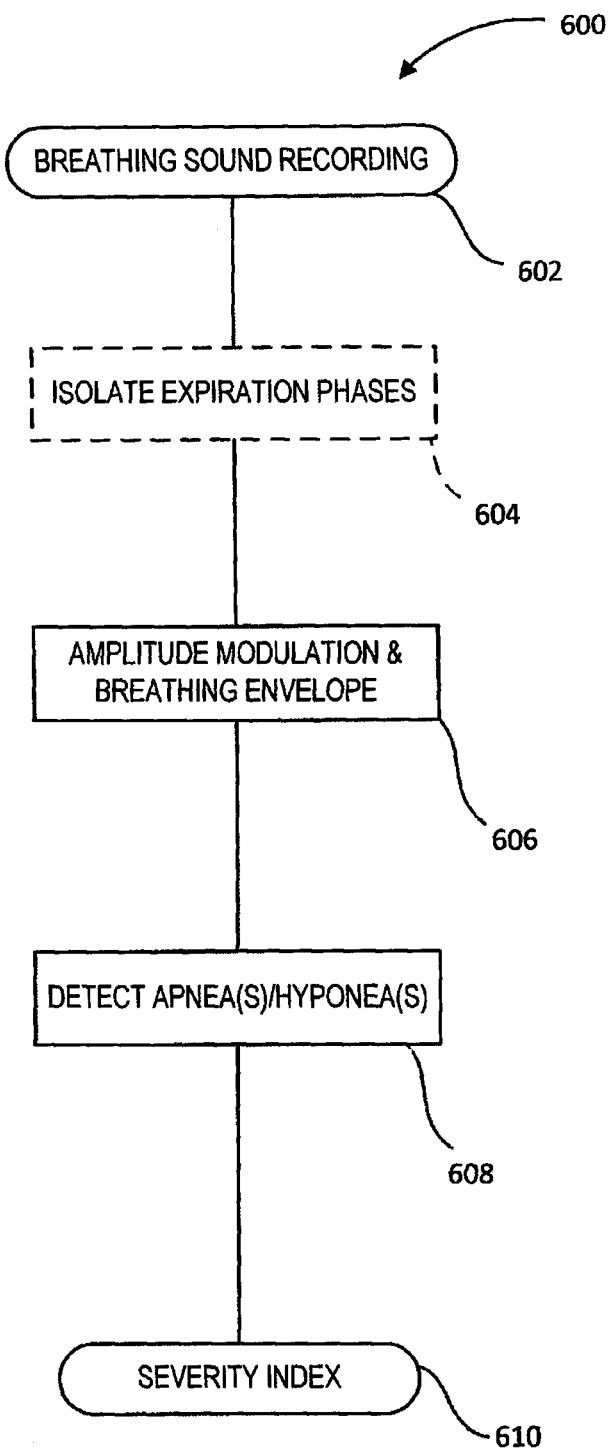
FIG. 6 is a high level flow diagram of a method for apnea and hypopnea detection, in accordance with one embodiment of the invention.

With reference to FIG. 6, and in accordance with one embodiment, a high level process 600 for detecting apneas and/or hypopnea will now be described. It should be noted that, while process 600 may, in accordance with one embodiment, ultimately allow for the provision of a severity index representative of a subject's breathing disorder, such as an AHI, the various sub-processes used in this classification may, in and of themselves, present usable results in identifying, characterizing and/or diagnosing a subject's breathing disorder(s), and that, without necessarily seeking to achieve the ultimate results considered by the overall process 600. Accordingly, while the following describes an overall breath disorder identification and qualification/quantification process, it will be appreciated that the scope of this disclosure should not be so limited, but rather, should be interpreted to include the various sub-process combinations that may lead, in and of themselves, to respective usable results in identifying and characterizing a subject's condition.

In this example, breath sound data is first acquired at step 602 via a mask having one or more transducers, such as described above with reference to FIGS. 1 to 4, operatively coupled to an integral, local and/or remote recording/processing device or module for processing the recorded breath sounds, for example as described above with reference to FIG. 5.

In a first (optional) step 604, breathing cycles are identified whereby timing data associated with successive inspiratory and expiratory phases can be extracted for use in segmenting the recorded data downstream to improve processing efficiency. In the exemplary embodiments described in greater detail below, expiration phases, in particular, are isolated and used downstream to further assess the subject's condition. Note that, while depicted in this example and described in greater detail below, this step is not necessarily required as other approaches may be implemented to identify data segments of interest. For example, the process may, in some embodiments, be implemented on the entire data set, particularly where expiration sound amplitudes are significantly greater than that of inspiration sounds, for example.

At step 606, the amplitude profile of the digitized recording, in this embodiment focused on expiratory sound amplitudes, is automatically extracted and scanned to identify events of interest, namely events over time possibly representative of respective apneic or hypopneic events. At step 608, one or more tests are implemented to automatically evaluate the prospective events extracted at step 606, and to characterize such events, as appropriate, as respective apneas and/or hypopneas. Different examples of event identification tests applicable in this context are discussed in greater detail below with reference to FIGS. 8, and 11 to 13. Identifying one or more events as representative of an apnea and/or hypopnea at step 608 provides a first indication as to the subject's condition. To further characterize the subject's condition, a severity index may also be calculated and output at step 610, in accordance with one embodiment, for example as a function of a number of events per preset time interval, such as an Apnea-Hypopnea Index (AHI) commonly utilized in the art to characterize a severity of a subject's condition. For example, in one embodiment, identification of at least five (5) or ten (10) apneic and/or hypopneic events per hour may be characterized as representative of a candidate having at least mild apnea, whereas higher counts may be subdivided into different classes such as high or severe cases of apnea. Based on this result, a tested candidate may receive treatment or recommendations, or again be directed to further testing, screening and/or diagnostics.

The process 600 will now be described with reference to exemplary implementations of each sub-process, as detailed below.

In this particular example, the breathing sound recording is analyzed at step 604 to automatically identify breathing phases, for example to identify timing data representative of each inspiration and expiration cycle of the subject's breathing track, which timing data can then be used in subsequent processing steps, for example in isolating expiratory sounds. In this particular example, breathing cycle identification is automatically implemented by the method described in International Application Publication No. WO 2010/054481, the entire contents of which are hereby incorporated herein by reference.

Briefly, an acoustic data waveform plot, for example as shown in the waveform versus time plot 700 of FIG. 7A for a single breath showing both an inspiration phase 702 and an expiration phase 704, can be processed using this method to automatically extract therefrom an indication as to each inspiratory and expiratory breathing cycle. In particular, a spectral analysis of the acoustic data, for example as shown by the exemplary FFT spectra of FIGS. 7B and 7C for respective time segments of the inspiration phase 702 and expiration phase 704 of FIG. 7A, can be used to achieve this result. As can be seen in FIG. 7B in respect of the inspiration phase, a sharp narrow band of harmonics is identified below 200 Hz and another peak is again identified above 400 Hz. Comparatively, the expiratory spectrum, as shown in FIG. 7C, forms a wider band that spans frequencies up to 500 Hz whose power drops off rapidly above this frequency.

Using this observed distinction between spectral compositions for inspiration and expiration data, appropriate frequency-domain metrics can be formulated to automatically distinguish the two types of phases. For example, in this particular embodiment, the bands ratio (BR) of summed frequency magnitudes between 400 to 1000 Hz, to frequency magnitudes between 10 to 400 Hz can be calculated for successive time segments of the recorded data to automatically identify inspiratory and expiratory phases, where higher BR values represent inspiration phases as compared to expiration phases. The following equation provides an exemplary approach to calculating the BR for a given time segment:

$$BR = \sum_{400\,Hz}^{1000\,Hz} FFT(f) \bigg/ \sum_{10\,Hz}^{400\,Hz} FFT(f)$$

where the numerator represents the sum of FFT higher frequency magnitude bins which lie between 400 and 1000 Hz, and the denominator represents the sum of FFT lower frequency magnitude bins which lie between 10 and 400 Hz, for example. Upon setting appropriate BR values for inspiration and expiration cycles, determined generally or with respect to a particular subject or class of subjects, automated breathing cycle identification can be implemented.

The person of ordinary skill in the art will appreciate that while the above describes one example of an automated approach to breathing cycle identification via breath sound analysis, other techniques, not necessarily limited to breathing sound analyses, may also be considered herein to achieve a similar effect, and that, without departing from the general scope and nature of the present disclosure. For example, other automated techniques achieved via the capture and processing of complimentary data, such as via Respiratory Inductance Plethysmography (RIP), (Respitrace Ambulatory Monitoring Inc., White Plains, N.Y., USA), which provides thoracoabdominal displacement data representative of changes of tidal volume during respiration, can also or alternatively be used to compliment further processing. Alternatively, visual identification of breathing phases may be implemented by a trained technician, albeit at the expense of some system automation.

As shown in FIG. 6, and in accordance with one embodiment, expiratory data may be used at steps 606 and 608 to detect, count and ultimately contribute to the characterization of a subject's manifested apneas/hypopneas. As will be described below, while expiratory data is predominantly used to achieve the intended results of this sub-process, inspiratory data need not necessarily be extracted. In the context of the overall process 600, where breathing cycle differentiation is readily accessible, such information may nonetheless be used to refine subsequent process steps.

In particular, steps 606 and 608 provide for the detection and identification of distinct apneic and hypopneic events for the purpose of characterizing the subject's breathing disorder(s) and providing adequate treatment therefor.

Figure 8:
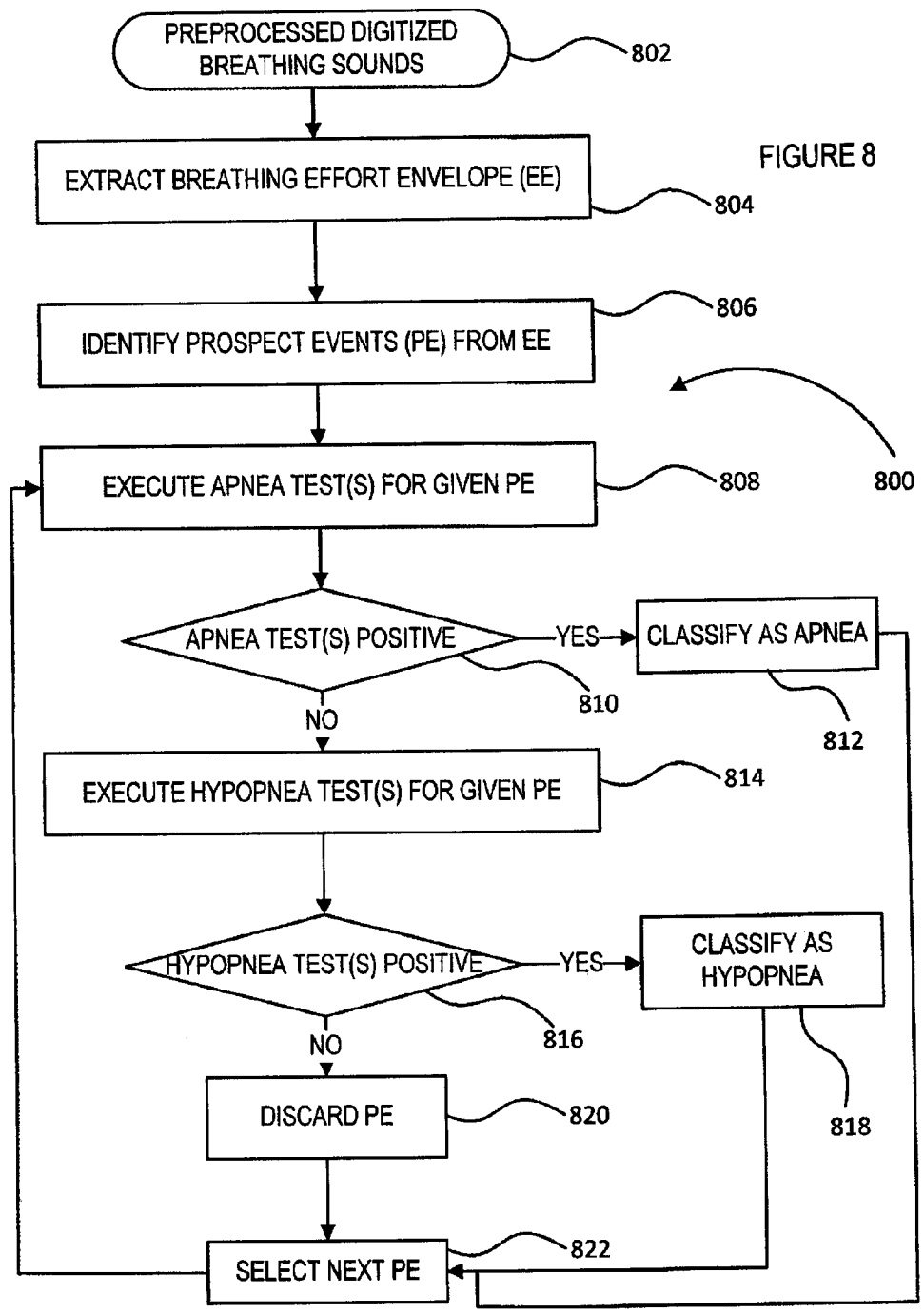
FIG. 8 is a high level flowchart of a method for identifying apneas and hypopneas from digitized breathing sounds, in accordance with one embodiment of the invention.
Figure 9:
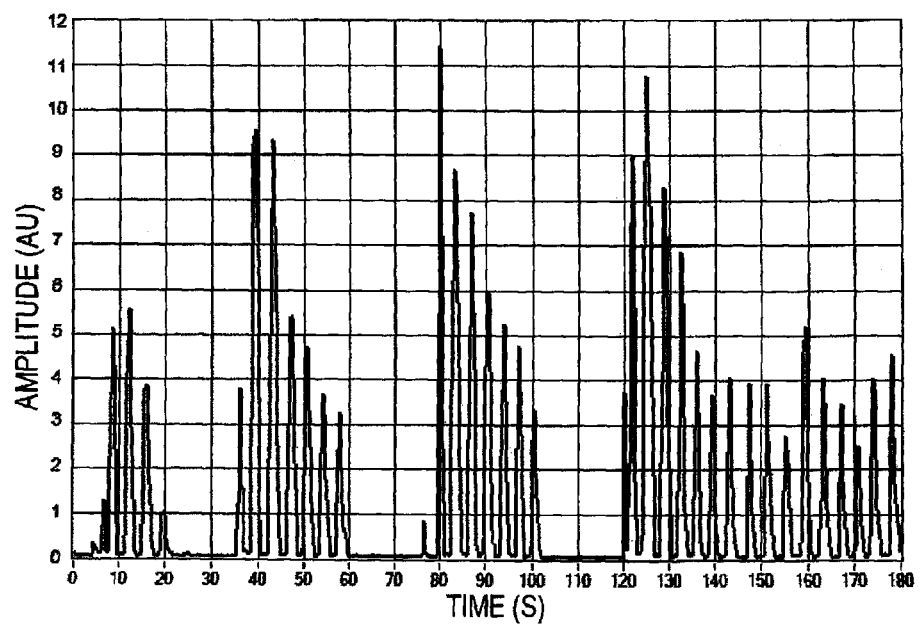
FIG. 9 is a plot of exemplary ventilation breathing sounds and apneic periods, represented by a train of digitized signal peaks, in accordance with one embodiment of the invention.

With reference now to FIG. 8, an example of a sub-process implemented in the context of steps 606 and 608 of FIG. 6, will now be described. In particular, this example provides one embodiment of an apnea and hypopnea detection method based on a recording of breathing sounds. In general terms, the method 800 is configured to automatically evaluate or recognize patterns in breathing sound data, which in one example described below, has been preprocessed to allow for digitization, outlier removal and normalization. For example, and as will be described in greater detail below, the raw breathing sound recording (e.g. see plot 130 of FIG. 1), can be digitized and the breathing envelope (BE) of each breath identified, for example as seen in FIG. 9 showing a series of breaths and apnea cycles within a 3 minute recording.

As will also be further described below, the digitized train of peaks obtained through initial preprocessing, and as shown in FIG. 10A, may be further adjusted to remove outlinear peaks whereby sharp spikes associated with unwanted sounds (such as coughs/snorting) can be removed (e.g. see sharp spikes of FIG. 10A removed in FIG. 10B). To facilitate evaluation of the resulting train of peaks, the data may be further normalized, for example via a segment-based normalization process such as an adaptive segmentation process, thus providing the preprocessed train of breath-related peaks shown in FIG. 10C. As will be appreciated by the skilled artisan, other preprocessing approaches may be applied to raw breathing sound data in order to ready this data for processing in accordance with the herein described apnea and/or hypopnea detection methods, and that, without departing from the general scope and nature of the present disclosure.

Figure 11:
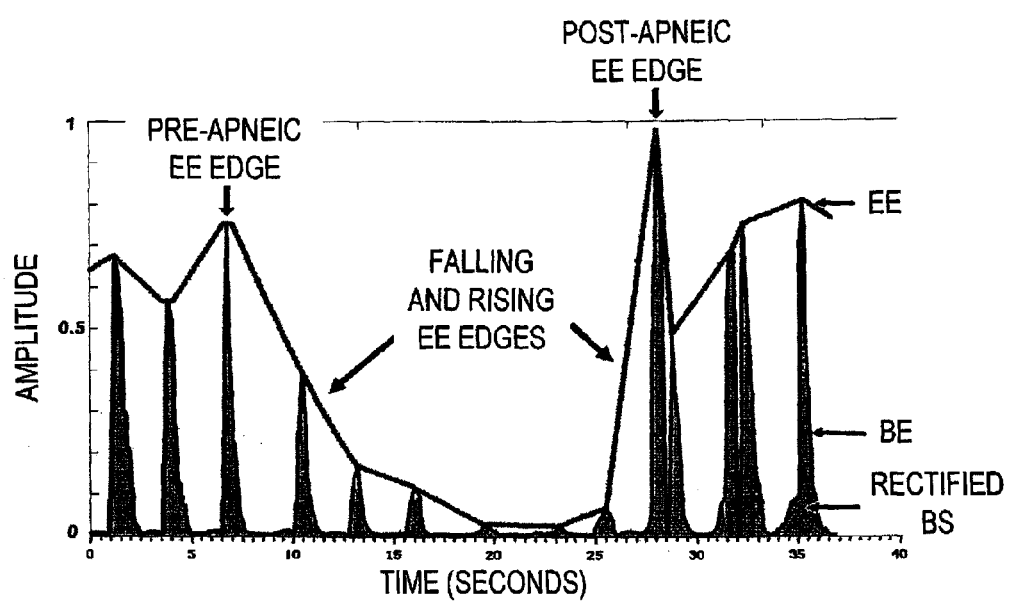
FIG. 11 is an exemplary plot of an identified prospect event (PE) showing relation between rectified digitized breathing sounds (BS) and a breathing envelope (BE) thereof, as well as an extracted breathing effort envelope (EE) taken therefrom and its various components, in accordance with one embodiment of the invention.

From the digitized breathing sound recording, shown as step 802 in FIG. 8 and which may be preprocessed in one embodiment in accordance with the above or other data preprocessing techniques, a breathing effort envelope (EE) is extracted (step 804), for example, as shown in FIG. 11, from which distinct apneic and/or hypopneic events may be identified, in accordance with different embodiments of the invention. The term "breathing effort" is used herein for the sake of illustration, and will be understood by the skilled artisan to represent, in accordance with different embodiments of the invention, a breath-to-breath breathing amplitude profile or variation over time, indicative of a breathing depth for example (e.g. deep breathing vs. shallow breathing), not to be confused with the depth criteria discussed below in identifying true apneas and/or hypopneas.

In one embodiment, prospect events (PE) are first identified in the EE at step 806, which PEs may then each be further evaluated for identification as a true apneic or hypopneic event. An example of a PE is shown in FIG. 11, wherein a significant drop in the EE may be automatically identified, in accordance with one embodiment, and retained as a PE for further evaluation.

For each PE, one or more apnea-specific tests are executed at step 808. Upon a given PE satisfying the requirements of this/these test(s) at step 810, this PE is automatically classified as a true apnea at step 812, which classification may later be used for further processing, or again in obtaining a count of total apneas within a given period or sleep cycle, for example.

Upon a given PE failing at least one of the requirements of the apnea-specific test(s) at step 810, one or more hypopnea-specific tests may then be executed at step 814 to evaluate whether this particular event is rather indicative of a hypopnea. Upon this PE satisfying the requirements of this/these hypopnea test(s) at step 816, this PE is automatically classified as a true hypopnea at step 818, which classification may later be used for further processing, or again in obtaining a count of total apneas within a given period or sleep cycle, for example. Otherwise, the PE is discarded at step 820 and the process repeated for the next PE at step 822. It will be appreciated that each PE may be processed sequentially or in parallel, and that, either for apnea and hypopnea consecutively for each PE, or distinctly for all PEs as a group.

Figure 14A:
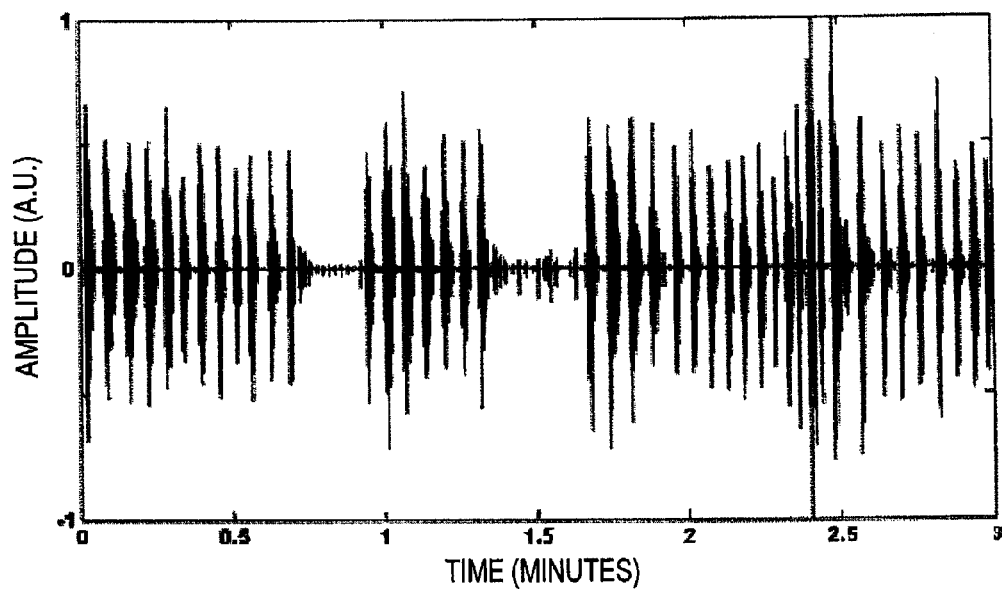
FIGS. 14A and 14B are plots of a three minute segment of sample breath sound data showing raw waveform and envelope profile data respectively.
Figure 14B:
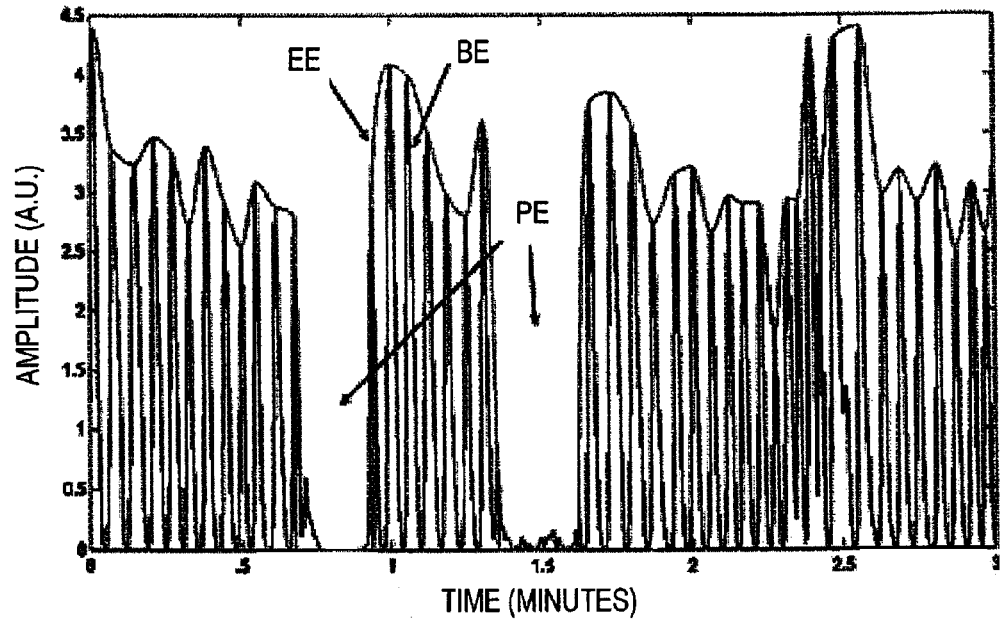

To further illustrate the above-introduced notions, and in accordance with a specific example, FIG. 14A provides an example of a three-minute segment of a raw acoustic signal waveform, acquired as described above, whereas FIG. 14B provides a plot of the breathing envelope (BE) and effort envelope (EE) for this segment emphasizing two PEs automatically identifiable from the extracted EE. As illustrated in these Figures, the raw acoustic signal acquired is efficiently converted into waveforms or profiles representative of the general breath sound amplitude. As noted above, adaptive segmentation and normalization techniques were used to preprocess the data, whereby transient outliers (e.g. coughs and snorting) and non-breathing components from the acoustic signal were excluded prior to generating the signal envelopes depicted in FIG. 14B. Namely, FIG. 14B depicts the envelope of individual breaths (BE), which is formed in this example by the summation of absolute values of signal points within 500 ms long moving windows. It consists of a train of peaks each representing a breathing cycle proportional to its amplitude. FIG. 14B also depicts the breathing effort envelope (EE) extracted therefrom, which effectively traces the overall changes or profile in the acoustic waveform from which respective apneas and/or hypopneas can be automatically identified. Namely, BE maxima are interpolated, and with outliers removed, the EE is normalized to establish a uniform baseline from which individual apneas and/or hypopneas can be automatically identified.

Figure 12:
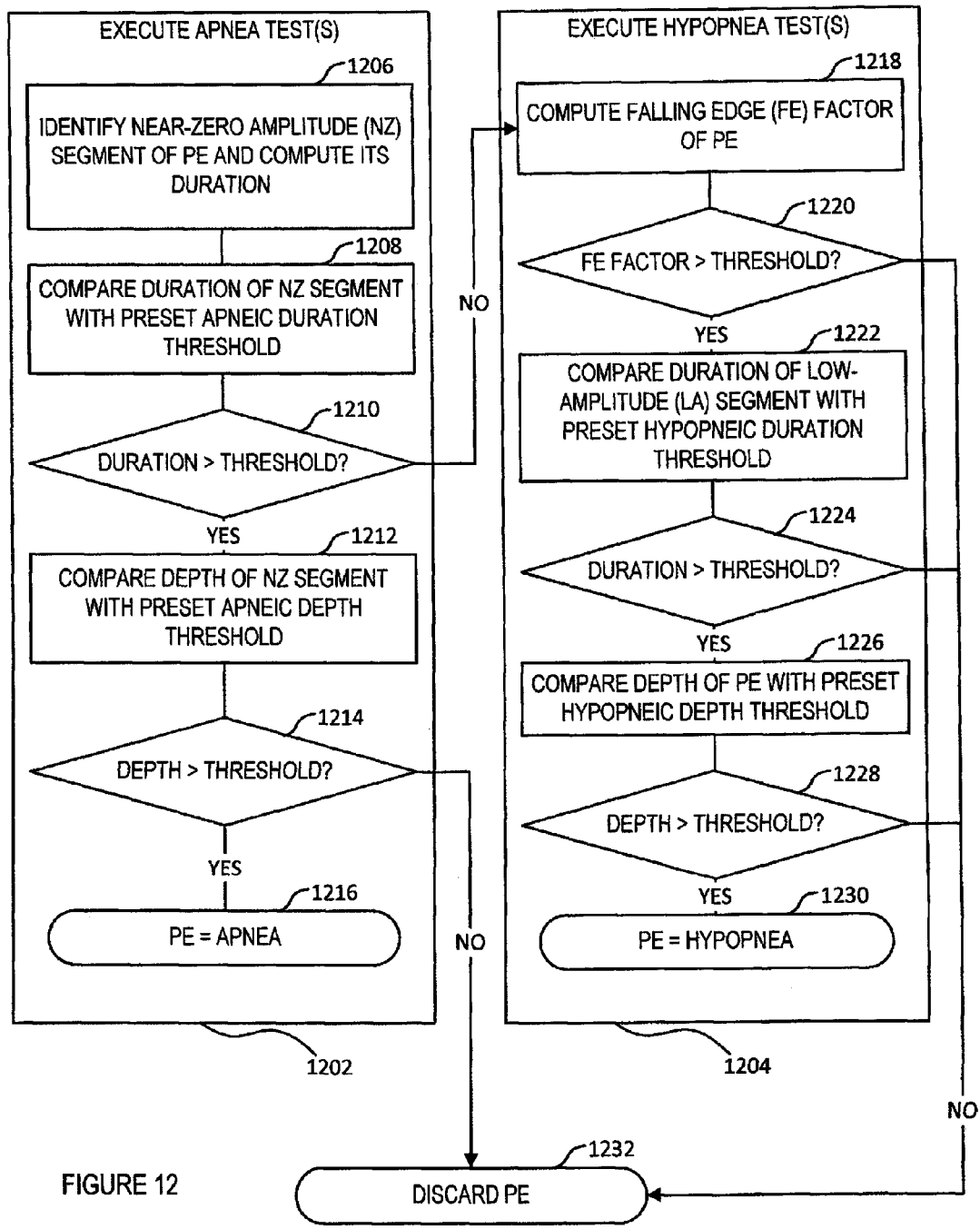
FIG. 12 is a flowchart of illustrative apnea and hypopnea tests executed within the context of the method of FIG. 8, in accordance with one embodiment of the invention.
Figure 15A:
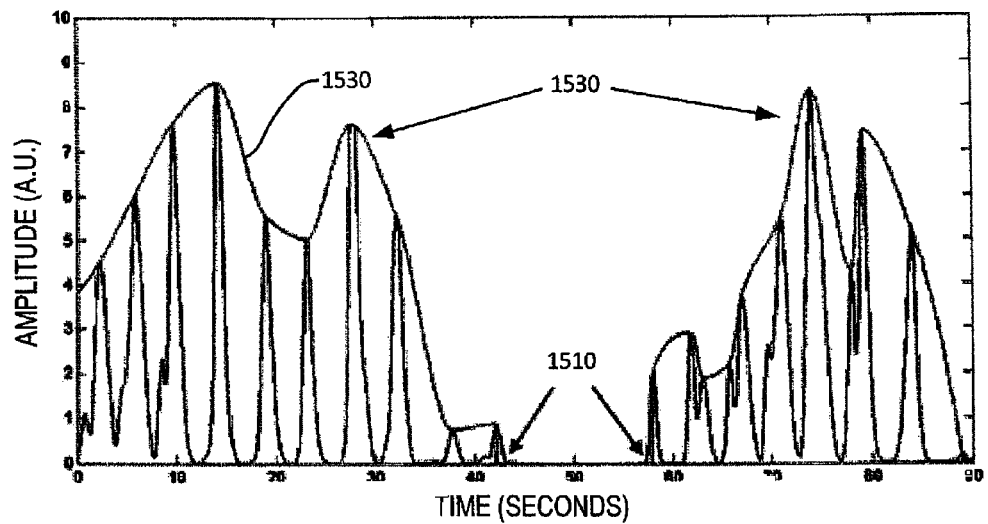
FIGS. 15A and 15B are plots of illustrative envelope profile data for an apneic and a hypopneic event, respectively.

FIG. 12 provides, in accordance with one illustrative embodiment, an example of particular automated apnea-specific 1202 and hypopnea-specific 1204 data evaluation methods, to be considered in the context of the method shown in FIG. 8. In this example, the apnea-specific tests are first executed, consisting of the following evaluations. First, the PE is evaluated at step 1206 to identify a near-zero amplitude segment, consistent with apnea. The duration of this non-zero segment is then computed and compared at step 1208 with a preset apneic event duration threshold. If the computed duration is greater than this threshold, determined at step 1210, the process proceeds to the next step 1212 of evaluating the depth of the near-zero segment relative to surrounding data, and comparing this depth with a preset apneic event depth threshold (e.g. an apnea specific minimum depth threshold). Upon the depth being identified at step 1214 as greater than the preset threshold therefor, the PE is classified as a true apnea at step 1216. FIG. 15A provides an example of a PE satisfying both apnea-specific criteria, whereby the duration of the substantially flat segment 1510 identified from the EE 1520, and the depth thereof in comparison with surrounding data (i.e. peaks 1530 delineating PE), satisfy preset thresholds therefor.

Figure 15B:
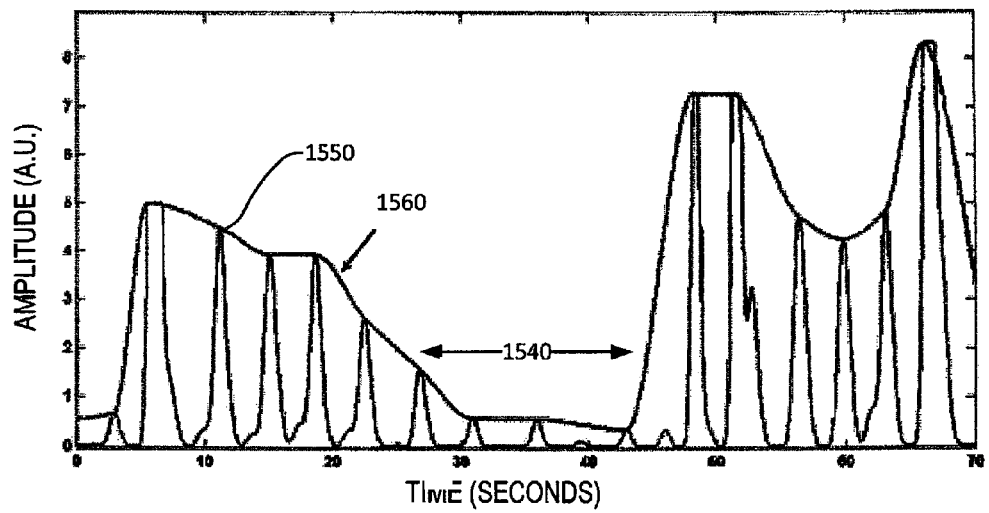
Figure 16:
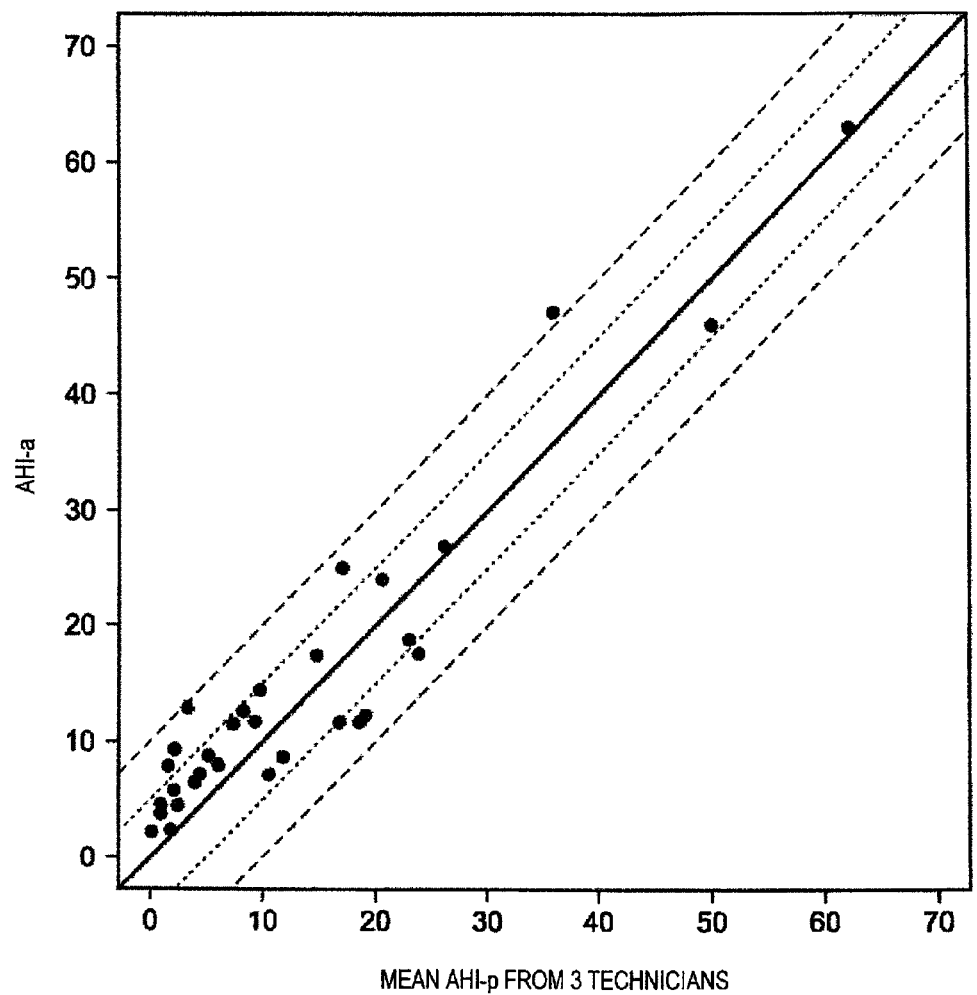
FIG. 16 is a plot depicting high level of agreement between Apnea-Hypopnea Index (AHI) as achieved using a method according to one embodiment of the invention (AHI-a), and AHI as measured by practitioners using a conventional PSG method (AHI-p)

On the other hand, upon the PE data failing at least one of the apnea-specific tests (steps 1210/1214), the process may be redirected to execution of distinct hypopnea-specific tests to rather qualify if the PE is indicative of a hypopnea event. In this example, however, where the PE passes the apnea duration test 1212 but fails the apnea depth test 1214, the PE is automatically discarded (1232) without proceeding to the hypopnea detection subroutine 1204. Where the PE first fails the apnea duration test 1212, the PE is evaluated at step 1218 to compute a falling edge factor thereof, which is generally indicative of a rate of amplitude decrease over time (e.g. decreasing gradient) for the selected PE (see FIG. 11). Upon the falling edge factor exceeding a preset threshold therefor, as determined at step 1220 (e.g. differentiating the dip from what may otherwise be representative of a comparatively healthy breathing cycle variation), a duration of a low-amplitude segment of the PE is computed (e.g. effective duration of the EE dip) and compared at step 1222 to a preset threshold therefor. Upon the computed duration exceeding the prescribed threshold, as determined at step 1224, a depth of the low-amplitude segment is then calculated and again compared at step 1226 with a preset requirement for consistency with a hypopneic event (e.g. a minimum hypopnea-specific depth threshold set shallower than the above noted minimum apnea-specific depth threshold). Upon satisfying each of these requirements, as determined at step 1228, the PE is classified as a true hypopnea at step 1230, otherwise, upon the PE failing any of these requirements, the PE is discarded at step 1232. FIG. 15B provides an example of a PE satisfying all hypopnea-specific criteria, whereby the characteristics of the low-amplitude segment 1540 identified from the EE 1550, and that of the falling edge 1560, satisfy preset thresholds therefor.

Figure 13:
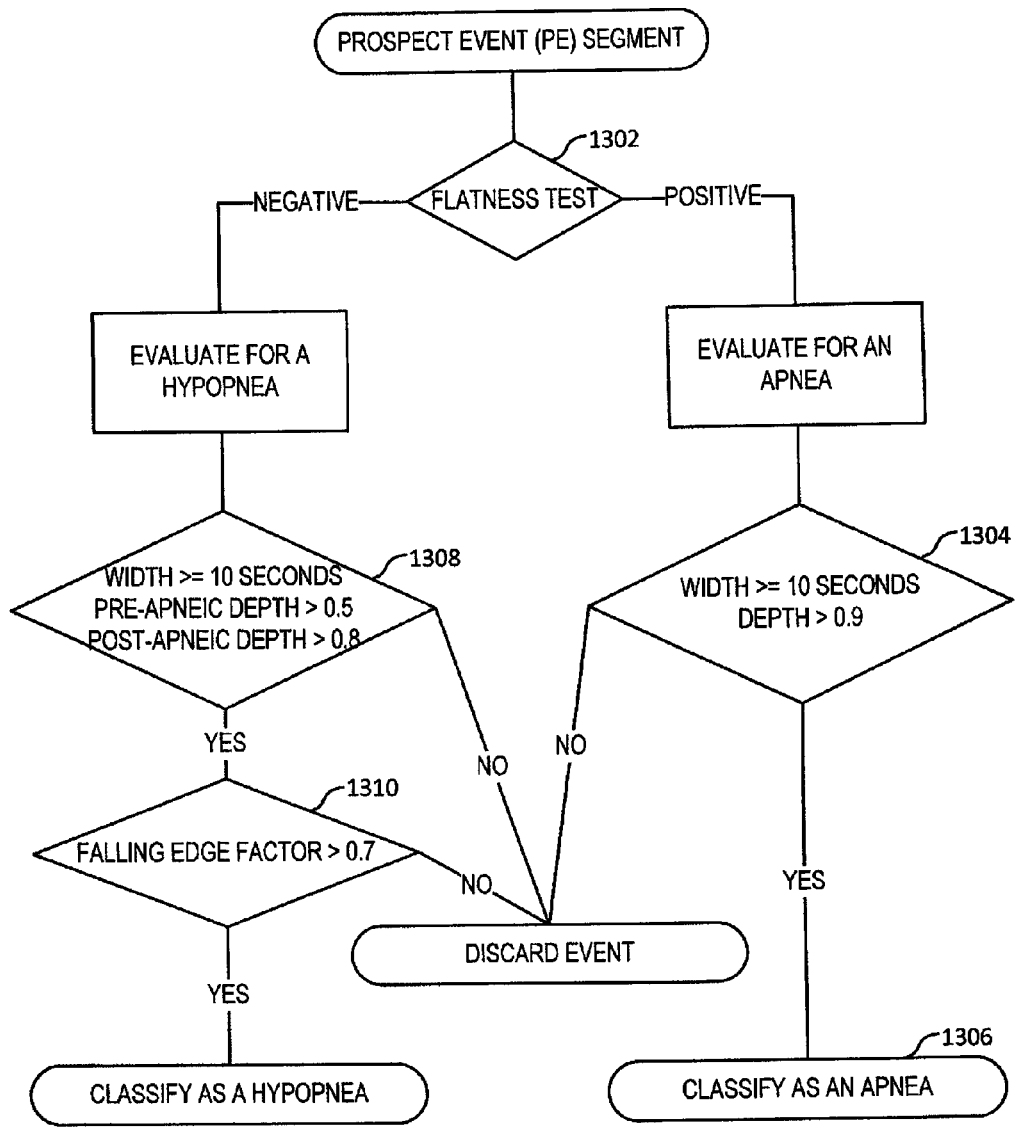
FIG. 13 is a flowchart of an exemplary method for classifying apneas and hypopneas from identified prospect events, in accordance with one embodiment of the invention.

FIG. 13 provides a specific example of a method for detecting apneas and hypopneas, in accordance with an embodiment of the invention, which method was used in validating the efficiency and accuracy of this method, as discussed hereinbelow.

To develop and validate the above-described and below-detailed methods, and in accordance with one embodiment of the invention, a series of patients suspected of sleep apnea were tested, and their results analyzed in accordance with the below-described method. Namely, for the results discussed below, 50 consecutive patients of at least 18 years of age that were referred to a sleep laboratory due to snoring or suspected sleep apnea, were tested both using the below-described method and by standard measures so as to validate the results discussed below. No exclusion criteria were imposed and subjects refrained from alcohol, sedative medications and caffeine for 12 hours before sleep studies.

In this particular example, subjects underwent overnight sleep studies using standard techniques and scoring criteria for sleep stages and arousals from sleep. All subjects slept with one pillow and with the bed flat. Thoracoabdominal movements and tidal volume were measured by respiratory inductance plethysmography, and airflow by nasal pressure cannulas. Arterial oxyhemoglobin saturation was monitored by oximetry. Obstructive apneas and hypopneas were defined as per standard methods as a cessation of tidal volume and at least a 50% reduction in tidal volume from baseline but above zero, respectively, lasting at least 10 seconds with out-of-phase thoracoabdominal motion or flow limitation on the nasal pressure tracing.

Apneas and hypopneas were scored according to 2 different criteria. The first was the American Academy of Sleep Medicine (AASM) criteria which defines an apnea as a drop in the respiratory signal, in this study thoracoabdominal movement, by ≥90% lasting ≥10 seconds, and a hypopnea as an event that satisfies either of the following 2 conditions: a drop of respiratory signal (from RIP in this case) by ≥30% lasting ≥10 seconds and accompanied by either a ≥4% desaturation, or a drop of respiratory signal by ≥50% lasting ≥10 seconds and accompanied by either a ≥3% desaturation or terminated by an arousal. These are not mutually exclusive. For the second criteria, apneas were similarly defined, but hypopneas were defined as a 50% to 90% reduction in tidal volume from baseline from the sum channel of the RIP tracing lasting ≥10 seconds, regardless of any desaturation or arousal, which criteria are referred to hereinafter as TV50. The AHI was quantified as the number of apneas and hypopneas per hour of sleep time.

For the purpose of comparative breath sound analysis, in accordance with one embodiment of the invention, breath sound data was also recorded for these subjects by a cardioid condenser microphone (Audi-Technica condenser microphone). The microphone's cardioid polar pattern reduces pickup of sounds from the sides and rear, improving isolation of the sound source. The microphone was embedded in the centre of a loose fitting full-face mask frame, for example as shown in FIGS. 1 to 4. As shown in these figures, the mask provided a structural frame to keep the microphone in a fixed location approximately 3 cm in front of the subject's face. Digitized sound data were transferred to a computer using a USB preamplifier and audio interface (M-Audio, Model MobilePre USB) with a sampling rate (Fs) of 22050 Hz and resolution of 16 bits. For the purpose of this study, the external audio interface was preferred over the regular built-in audio adapters because of its better Signal to Noise (S/N) ratio, which is 91 dB (typical, A-weighted), though it will be appreciated that either of these adapters, or others like them, may be used in different embodiments to produce similar results.

To ultimately detect reductions and/or interruptions in breathing (i.e. hypopneas and apneas), and in accordance with one embodiment, breath sound recordings were first analyzed to evaluate the temporal evolution of breath sound amplitude in these recordings. For this purpose, signal envelopes were created to detect overall changes in the amplitude of the acquired signal, (e.g. in the steps described below).

For example, in this embodiment, the breath sound signal amplitude envelope was extracted to preserve sharp transitions in the signal, which is a specificity of the signal in hand that could have sudden transitions from silence during an apnea to hyperventilation up on resumption of breathing. To do so, the following steps were followed.

Extracting Envelop of Individual Breaths (BE)

In this step, the recording is divided into non-overlapping segments, for example of 500 ms duration. Data points in each given segment are then summed to produce a single bin that represents the 500 ms segment. The length of the interval is chosen in order to balance between preserving short term details such as onset of inspiratory and expiratory phases, and longer term events such as apneas and hypopneas. Since the shortest breathing phase is generally 1.5 seconds in rapid normal breathing (i.e. 20 breaths/minute), a bin size/segment duration of about 500 ms, as in the present example, generally provides sufficient resolution to capture such breathing details. As will be appreciated by the skilled artisan, different bin/segment sizes may be considered herein without departing from the general scope and nature of the present disclosure. This person will however appreciate that overly extended segment intervals may have adverse results, for example in the merging of apnea borders and thus resulting in a false representation of the apnea's duration, or again in the merging of transient high amplitude outliers produced by coughing and snorting (transient load snoring) with surrounding signals thus making them more difficult to remove in subsequent steps.

The resulting signal is a train of peaks, each representing a breathing phase, which are interrupted by apneas as illustrated, for example, in the 3 minutes recording in FIG. 9.

Outlier Removal

While successive breaths do not tend to vary dramatically in amplitude, these may be interrupted by transients such as cough, or snorting (transient loud snoring). Such transients thus occasionally appear as outliner spikes in the envelope of individual breaths, as extracted in the previous step. Since such outliers can affect subsequent steps, it is generally preferable that they be removed.

In one embodiment, an outlier is defined for this purpose as high amplitude data points that exceed 4 standard deviations (4 σ) of the surrounding 180-second data segment, which segment length was selected in this particular embodiment in consideration of a general apnea cycle length. Namely, in patients with severe sleep apnea, breathing is present only roughly 50% of the time and is interrupted by apneas that are approximately 30 seconds in duration. Thus, approximately every 60 seconds, an alternating pattern of apnea and ventilation occurs repeatedly during sleep and this constitutes the basic unit of segmentation. In order to incorporate multiple patterns, a segmentation window of 180 seconds (=3×60) was chosen. As will be appreciated by the skilled artisan, this interval should be minimized as much as possible in order to avoid incorporation of meaningful long term change of breathing type, such as moving from quiet breathing to snoring, or the like.

In order to remove outliers, BE is segmented into short segments each of 180 s that overlap by 50%. All data points greater than 4 σ are truncated to 4 σ. It should be noted that, in the case of consecutive points that indicate the presence of outliers, the duration of these consecutive points should not exceed 5% of the length of the segment. Otherwise, the detected strong amplitude deviations are not considered outliers, as they could still contain physiologically relevant information.

Extracting Envelop of Breathing Effort

The next step is to trace the overall changes in waveform level. These changes are the result of apneas and hypopneas and also the change in breathing pattern. This is achieved by interpolating the waveform's maxima to extract the effort envelop (EE), as illustrated in FIGS. 11, 14 and 15. This particular envelop can then be used, as noted above and in accordance with different embodiments, to detect individual apneas and hypopneas.

Amplitude Normalization of EE

Figure 10:
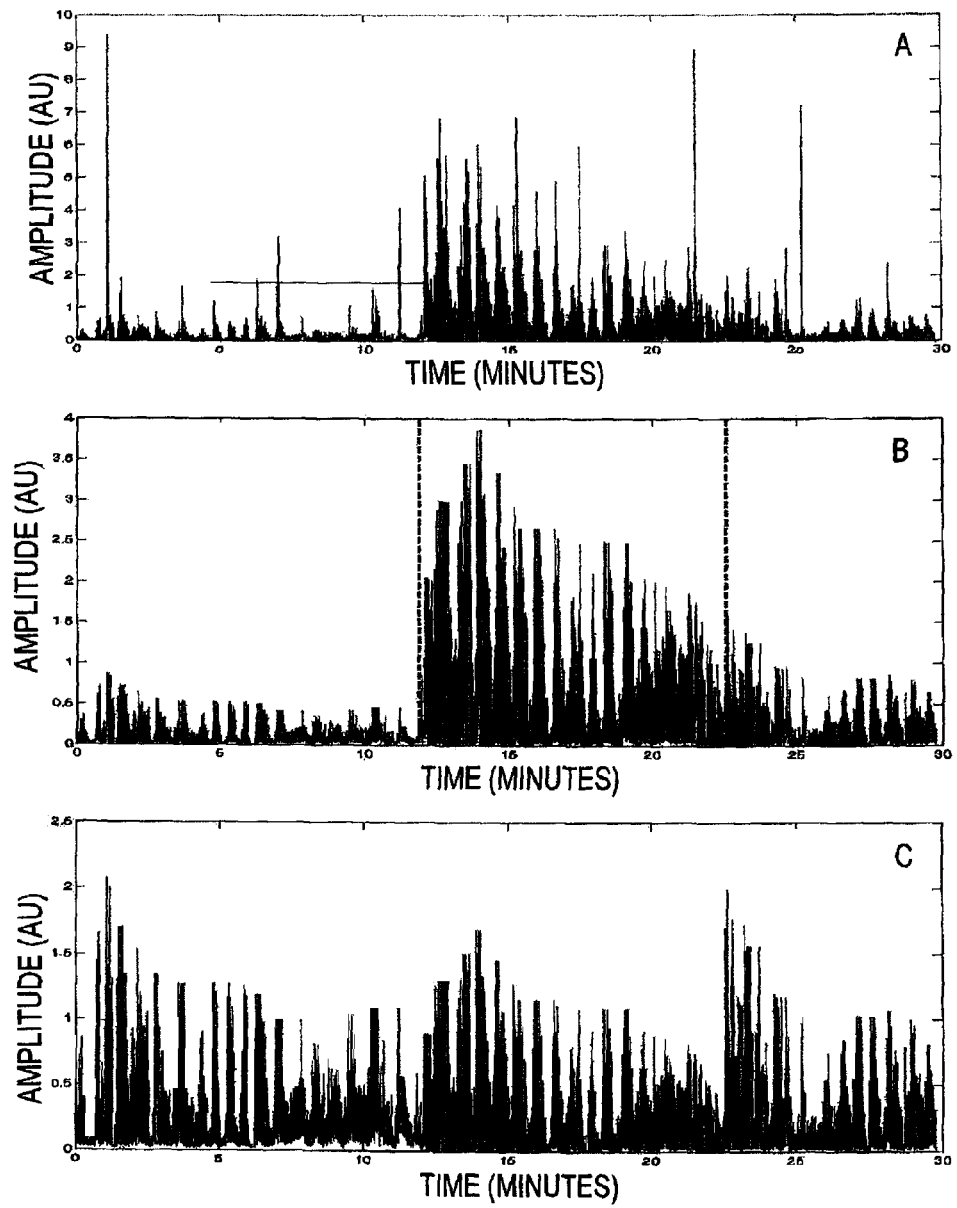

In order to improve the accuracy of apnea, and particularly hypopnea detection, which are represented by relative reductions of breathing effort, in one embodiment, the method uses a baseline level of breathing sounds as reference. Breath sounds, however, generally produce particularly dynamic and variable signals due to the occurrence of snoring and variations in breath types. This can thus result in long term variations in the overall amplitude of the EE that can obscure accurate detection of hypopneas for lack of a suitable reference baseline. Accordingly, and in accordance with one embodiment, an overall normalization of the signal's amplitude is provided in order to enhance hypopneic event detection. In one example, an adaptive segmentation method is used to provide such normalization, wherein borders between long-term varying levels are found so to then respectively normalize each of these levels to unity. This results in a substantially uniform amplitude of the breath sound signals over extended periods, yet preserving short term variation due to apneas and hypopneas. An example of this process is shown in FIG. 10, where the breathing envelope (BE) of the digitized breathing sound (BS) train in (A) is first cleaned of outliners to produce the BE in (B), which is then itself submitted to segment-based normalization as noted above to obtain the preprocessed BE (otherwise referred to as the BE of the rectified BS) in (C), from which preprocessed BE a more accurate breathing effort envelope (EE) may be extracted, as in FIG. 11.

Scanning for Prospect Apneic and Hypopneic Events

Using the preprocessed (i.e. normalized and outlier-free) EE, as produced in one embodiment following the above-described steps, apneic and hypopneic event detection may then be implemented. Namely, this preprocessed EE generally represents a trace of the overall breath sounds amplitude, from which characteristic patterns of apneas and hypopneas can be automatically identified.

In one embodiment, the signal is scanned to first identify prospect apnea/hypopnea events. For example, in one embodiment, valleys in the EE signal that are below a predefined threshold are first identified. For example, an empirical threshold of 0.4 of a standard deviation below the mean of EE has been shown to provide adequate results. Accordingly, this step allows for the detection of troughs in the signal that have sufficient depth to possibly correspond to an event of interest, while excluding negligible signal troughs that could more likely be attributed to breath-to-breath variation. In one embodiment, this amplitude profile is scanned for segments satisfying a minimum prospect event depth threshold, wherein this minimum prospect event depth threshold is at least as shallow as a minimum hypopnea event amplitude depth threshold.

In a following step, each identified valley is extracted from the main EE. This is achieved, in one embodiment, by extracting a 60 seconds long segment whose centre is the deepest point of the trough or the middle of the trough if it is a flat region. Hereafter, this segment is named prospect event apnea (PE). Each PE will generally contain a central trough in addition to proceeding and subsequent activities given that an apneic/hypopneic event generally lasts between 10-50 seconds. The activities that proceed or follow an event will thus also be used as criteria to detect true events of apnea and hypopnea.

Since the 60 seconds interval of a given PE may contain redundant data when the event's length is relatively short, an additional step can be used to delineate the borders of the event that correspond to normal breathing level. For example, in one embodiment, this step is achieved by selecting the closest peak to the centre on both sides that exceeds 50% of the maximum point of the PE. Using this two-step approach to PE border identification, the process both mimics human intuition in finding drops in breathing by comparing the levels of a given trough to immediately adjacent data, and accounts for subtle changes in breath sounds level that remain present despite the normalization and which would otherwise make border identification via comparisons with a universal level for the entire recording likely inaccurate.

In this embodiment, each PE is then normalized to unity by dividing it by its maximum and subtracting any offset so that the minimum point is zero. This step casts all PE's into a similar level range (0-1), as depicted in FIG. 11, thus facilitating subsequent processing steps.

Detection of True Apneas and Hypopneas

In order to detect true events, and in accordance with one embodiment, each PE is evaluated based on preset conditions. Since apneas and hypopneas differ in their nature, their manifestations in breath sounds are also generally different. For example, there is generally a complete collapse of the upper airway and the absence of breathing and breath sounds during an apnea. Also, pre and post apneic breaths are often relatively irregular, especially in OSA. On the other hand, hypopneas are often characterized by a partial collapse of the upper airway and a reduction of airflow by more than 50% but still remaining above zero. Thus, breath sounds may continue to occur during a hypopnea. Accordingly, in one embodiment, in order to identify and differentiate apneas and hypopneas, different preset conditions are applied to identify each type of event, and thus provide for enhanced diagnosis and improved treatment.

Tests for Apneas

In one embodiment, a set of criteria are applied to each PE to identify whether it qualifies as a full apnea. In general, such criteria seek to evaluate the presence of any substantially flat segment (step 1302), wherein, upon such flat segment satisfying both duration and depth criteria (step 1304), the PE is positively identified as an apneic event (step 1306). For example, flatness in the acoustic data generally corresponds to a lack of breath sounds, and can be evaluated by counting the number of zero or near-zero points in a given PE. If the number of those points corresponds to a preset time interval, or above, then an apneic event may be positively identified. In one embodiment, the preset time interval is set at 10 seconds, and the length of the flat segment is calculated as LApnea=Ts·||PE<0.01||, where ||PE<0.01|| denotes the length of a vector for which PE amplitude is below 0.01, and Ts is the sampling period (1/sampling frequency (Fs)).

To evaluate the depth of an identified flat segment, the amplitude of this segment is compared with the amplitude of the higher of the two apneic borders obtained in the previous step where prospect events are first identified. For example, in one embodiment, if the depth of a substantially flat segment as identified above is greater than 0.9, then the segment is deemed to identify a true apneic event. Accordingly, upon qualifying a given PE as comprising a sufficiently flat segment of sufficient depth, that particular PE is classified as an apnea and automatically counted as such.

Tests for Hypopneas

In the event that the above-described predefined apnea requirements are not met for a given PE, a distinct set of predefined hypopnea requirements may still be applied to account for any potential hypopneas. For example, in one embodiment, if the flatness test (step 1302) set out above comes back negative, e.g. where the computed length of an identified substantially flat segment is below the prescribed threshold, then this PE is passed on to next stage where hypopneic criteria may be applied to evaluate whether this PE rather represents a true hypopnea. In the current example, this set of criteria consists of a falling edge test, a width test, and a depth test (step 1308).

The falling edge test in this embodiment is based on the assumption that a hypopnea evolves as a gradual reduction in net airflow as a result of gradual collapse of the throat in the obstructive type, or gradual decrease in respiratory drive in the central type. This reduction, however, does not always manifest in an ideal smooth negative slope because of the variable nature of breath sounds on a breath-to-breath basis. Therefore, the falling edge test can be configured to take into consideration the non-linearity of the drop in breath sounds amplitude prior to the hypopnea, which may be achieved in accordance with the following steps:

1. The falling edge (FE) of the PE is extracted from the first point of the PE to its minimum point.
2. The derivative of FE is calculated as the difference between each point and the preceding point. The results are stored in an array. If FE is decreasing at all points, then the derivative will consist of negative values only. Positive elements of the array represent transient peaks during the overall drop of the breath sound level. The absolute value of the sum of all these points will thus give the difference between the first and last values of FE.
3. All the points in the FE derivative are summed up to get a single value and the sum of all positive numbers in the derivative is extracted from that value.
4. The result of step 3 is divided by the difference between the maximum and minimum point in FE. The absolute value of this result is called the falling edge factor. Since the minimum value is always zero because of the offset subtraction described earlier (PE normalization), it is sufficient to divide by the maximum point.

Based on the above, the falling edge factor can be obtained from the following equation:

$$\text{FE factor} = |\Sigma\Delta(FE) - \Sigma(\Delta(FE) > 0)| / \max(FE)$$

where $\Sigma$ denotes summation, $\Delta$ denotes discrete derivative, '>0' denotes positive elements of a vector, and $|\blacksquare|$ denotes the absolute value.

If the FE is decreasing at all points, then the sum of the derivative array elements is equal to the maximum of the FE, which is the starting point; thus the falling edge factor will be equal to 1. In this case, it will be interpreted that the breath sounds level decreased from the full loudness in normal breathing to the faintest level in the hypopnea in a completely gradual trend. On the other hand, if FE contains transient peaks, the FE derivative will contain positive values that will decrease the numerator of the above equation for the FE factor. Accordingly, the result will be less than 1 depending on the number of rises and their height, which are not consistent with a net gradual decrease in breathing effort. In order to differentiate, at step 1310, FE factors indicative of hypopnea from those more likely indicative of regular breathing, a predefined FE factor threshold is applied, whereby a FE factor computed above this threshold is maintained as indicative of a PE representative of a possible hypopnea, whereas a FE factor below this threshold automatically excludes this PE from a total hypopneic count. In this particular example, the preset FE factor was set at 0.7, which translates into a 70% decreasing trend or greater.

As noted above, however, the present example contemplates a three part test for accurately identifying a hypopneic event, whereby failure of any one of these tests results in the exclusion of a related PE from hypopneic counts. As a second criteria in this example, the PE is processed for compliance with a hypopneic width requirement (step 1308), which effectively provides for a measure of an effective PE duration as compared with a preset duration threshold, whereby an effective PE duration computed as being greater than the prescribed threshold may be indicative of a true hypopnea. In this example, the width test is performed by measuring the time interval (duration) between the FE and rising edge (RE) when at the lower quarter of the PE given by the equation:

$$\text{PE duration} = T_s \cdot \|PEIq\|$$

where PEIq denotes elements in the lower quarter of PE. In this embodiment, a measured PE duration greater or equal to 10 seconds is retained as a possible hypopnea, whereas shorter durations are rejected from hypopneic counts.

Again in accordance with this exemplary embodiment, a third test is applied consisting of a hypopneic depth test, which is similar to the one used to evaluate an apnea and calculated similarly as the difference between the maximum and minimum values of the PE, the latter being zero of course in a normalized PE. To compute this result, the maxima are taken at the start and end points of PE, wherein the starting peak represents the level of the pre-apneic breathing and the end peak represents post-apneic hyperventilation. In this example, a possible hypopneic event is identified where the starting peak measures at least 0.5, which is based on the 50% fall in breathing effort by definition of an apneic event. The end peak, on the other hand, corresponds to the post-apneic hyperventilation, which is higher in amplitude. Therefore, it stands to reason to expect that the end peak is higher than the start peak. Accordingly, in this example, a higher threshold of 0.8 is set for the post-apneic peak. As will be noted, the hypopneic thresholds are lower than that set for the apneic depth test, in which total cessation of breathing takes place, but high enough to substantially exclude false positive results. In this example, the combination of these three tests (falling edge, width, and depth criteria) were shown to encompass the specific physiological characteristics of hypopneas yet, remain sufficiently flexible to detect different forms that result from the dynamic nature of breath sounds.

Results of Comparative Study

As introduced above, in order to validate the performance of the above-described process, the results thereof were compared against results obtained by PSG, which currently represents the most accurate standards in the art. In making this comparison, the total number of the detected apneas and hypopneas from breath sounds was divided by the recording time to get the acoustic apnea-hypopnea index (AHI-a). This was compared with the polysomnographic apnea-hypopnea index (AHI-p), which is the frequency of apneas and hypopneas obtained from polysomnographic recordings divided by recording time. The AHI-p was evaluated according to the recording time rather than sleep time in order to simulate home recording of breath sounds where EEG will not be available.

As can be seen from the plots presented in FIGS. 16 to 19, results obtained in accordance with the above-described method are consistent with those independently obtained via PSG, thus validating the efficiency and accuracy of the herein-disclosed embodiments relying on breathing sound analysis.

For instance, in the above-described example, the acoustic (i.e. breathing sound-based) apnea-hypopnea index (AHI-a) was calculated automatically from acquired data and compared to the average of three AHI-p values. As can be seen from FIG. 16, acoustic AHI showed 95% agreement with the mean PSG AHI of 3 scorers ($R^2=0.90$). In this Figure, a solid reference line is drawn to represent equality of the acoustic and standard AHI measures and dashed reference lines are drawn at differences of 5 and 10 points. It can be seen that the acoustic AHI lies within 10 points of the average AM for all but one subject. It can also be seen that for small AHI values (<15), most acoustic AHI values lie within 5 points of the mean for the standard AHI.

To further evaluate the performance of the above-proposed methods, the AHI obtained from acoustic recordings (AHI-a) was further compared with that obtained from PSG (AHI-p) while accounting for the fact that the AHI-p is obtained by a technician visually scoring the PSG recordings, raising the possibility of scoring variability between technicians for the same PSG. To determine the degree of inter-rater variability in the scoring of the AHI, 3 experienced sleep technologists scored the AHI of each of the 50 patients, blinded to the score of the other technicians and to the AHI-a. Similarly, the AHI-a was determined automatically without knowledge of the AHI-p.

Since the AHI-p scores of the 3 technicians represent the reference standard, the degree of agreement was assessed amongst the 3 technicians prior to comparison with the AHI-a. The inter-rater reliability among the 3 technicians and its 95% confidence interval were calculated using the know Analysis of Variance (ANOVA) method.

The degree of agreement between the 2 methods was assessed by Pearson correlation and Bland-Altman tests. For those tests, the AHI was evaluated according to the time-in-bed period rather than sleep time to simulate home recordings of breath sounds where sleep stages are not recorded. Correlation coefficients with all 3 scorers were calculated using pairwise differences in Pearson correlation and using bootstrap (n=2000) to obtain the 95% confidence interval (CI).

To test the ability of acoustic analysis to distinguish between the presence or absence of SA, the accuracy, sensitivity, specificity, positive and negative predictive values, and positive and negative likelihood ratios were calculated. These were first calculated according to time-in-bed for both AHI-a and AHI-p, and then, according to time-in-bed for AHI-a and sleep time for AHI-p.

Figure 17A:
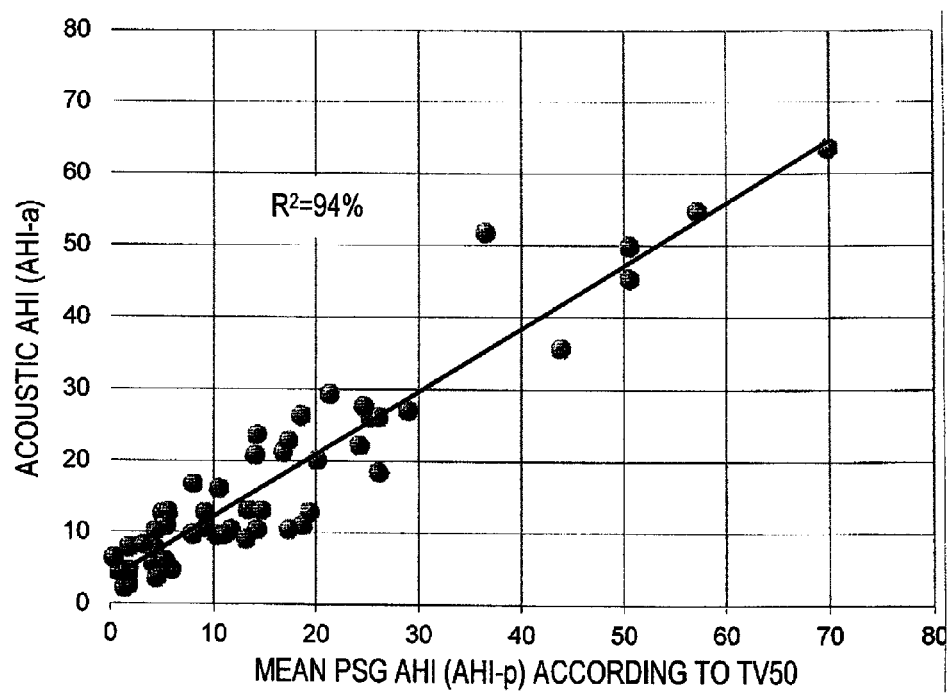
FIGS. 17A and 17B are plots showing a distribution of AHI-a and 3 AHI-p scores as a function of the mean AHI-p score, obtained according TV50 and AASM standards, respectively.
Figure 17B:
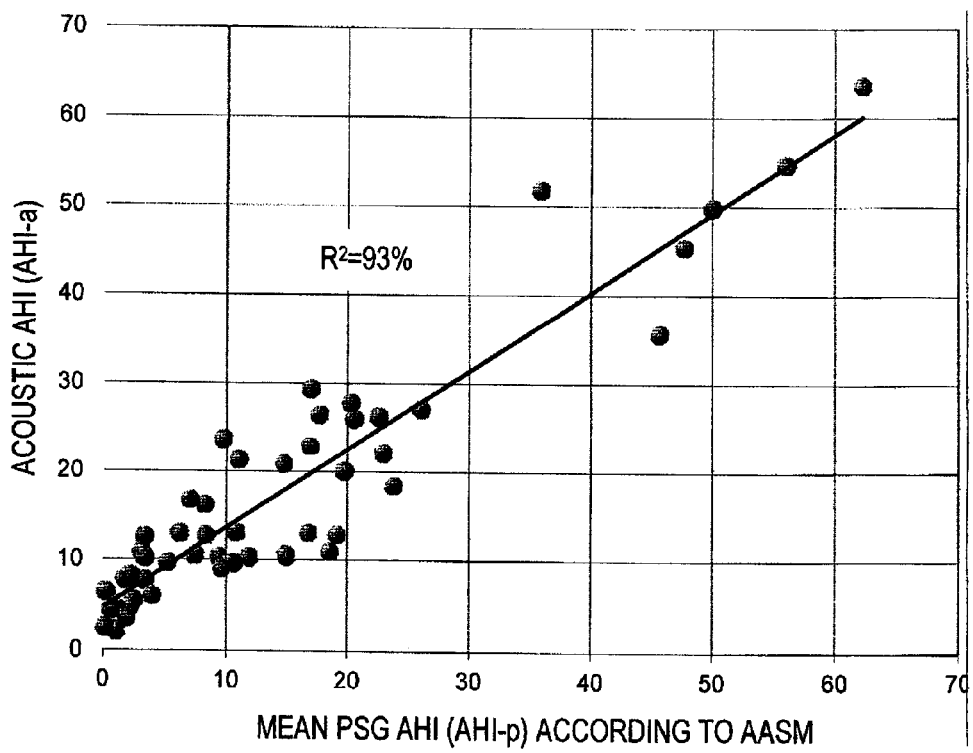

In comparing AHI-a and AHI-p, a strong correlation was identified with a mean R=0.94 and a 95% CI of 0.87-0.97 according to TV50 criteria, and a mean R=0.93 and 95% CI of 0.85-0.96 according to AASM criteria. FIG. 17 displays the distribution of the AHI-p scored by each of the 3 technicians and the relationship between the AHI-a and the mean AHI-p for TV50 (A) and AASM (B).

Figure 18:
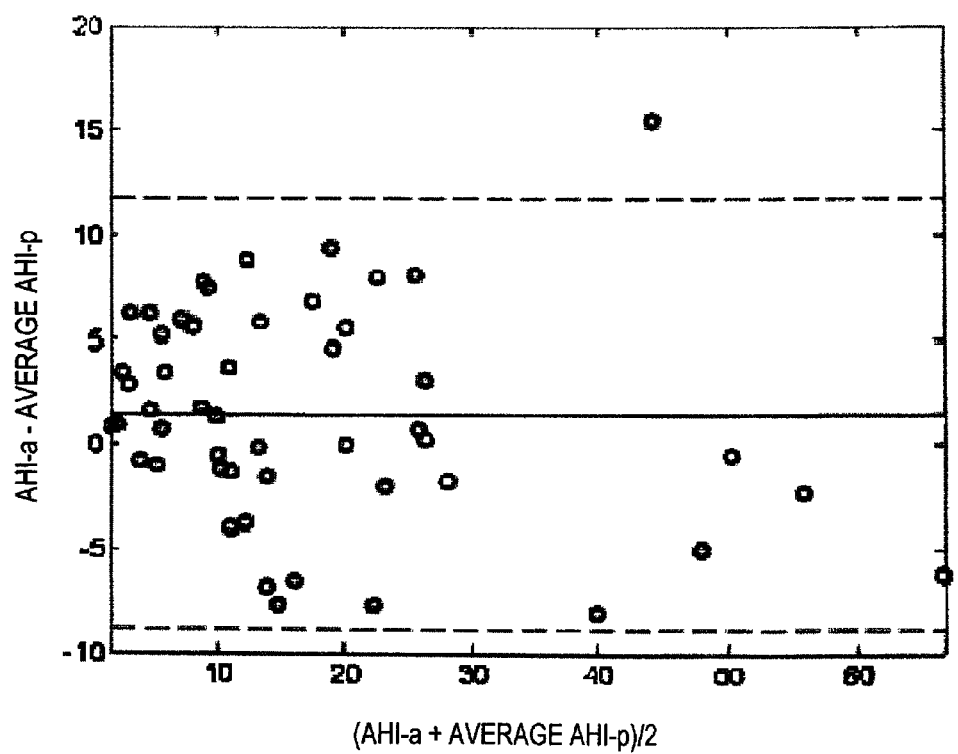
FIG. 18 is a Bland Altman plot showing scores falling within Limits of Agreement with respect to AHI-p scores.

The Bland-Altman limits of agreement were calculated to assess agreement between the AHI-a and the AHI-p of each of the three technicians and the mean of all three. Forty nine of the 50 AHI-a (98%) fell within the limits of agreement of the AHI-p for TV50 as shown in FIG. 18. Similarly, 96%, 96%, and 98% of AHI-a scores fell within the limits of agreement of AHI-p scored by technicians 1, 2, and 3, respectively. The proportion of AHI-a scores that fell within the limits of agreement of PSG-p according to AASM was 92%, 94%, 92%, and 92% in comparison with technicians 1, 2, 3, and their mean scores, respectively.

According to the criterion set in the present example, a diagnosis of SA is made if the AHI≥10, whereas SA is ruled out if the AHI<10. In comparing the diagnosis of SA based on AHI-a to that based on the three AHI-p, a decision rule for combining the diagnoses from the 3 technicians was obtained. Two approaches were considered in doing so. First, a diagnosis was considered based on the average of the three technicians, such that SA was positively identified if the mean score was ≥10. Second, a diagnosis was considered based on the agreement of AHI-a with at least one technician. In this case, if AHI-a≥10 and at least one of the three AHI-p≥10, then the AHI-a diagnosis of SA is considered to be a true positive, whereas a false positive ensues if AHI-a≥10 and all three AHI-p<10. The same concept was applied to true negative and false negative values. The rationale behind investigating this approach was that the agreement of the acoustic analysis with one technician indicates that the first lies within the range of inherent variability among different human scorers, which could indeed result in fluctuations of scores around the nominal cut-off of AHI≥10 among the technicians themselves.

The comparisons of diagnostic accuracy of the AHI-a compared to either the mean of the three AHI-p values, or compared to the AHI-p scored by one or more technicians using TV50 or AASM criteria are presented in Table 1 and Table 2, below. Considering that the agreement with at least one technician incorporates the range of the three scores for the same subject, it factors in the inter-rater variability around the nominal cut-off point. When comparing agreement with at least one of the three technicians, validity measures were 100%, 73%, and 88% for sensitivity, specificity, and accuracy, respectively, according to TV50. When comparing against the mean AHI-p those dropped to 95%, 69%, and 84% (Table 1). These values were comparable but slightly lower when comparing AHI-a against AHI-p according to AASM criteria (Table 2).

TABLE 1

Diagnostic agreement according to TV50 scoring criteria.

| According to 1 or more technicians | | According to mean AHI-p | |
|---|---|---|---|
| Sensitivity | 100% | Sensitivity | 95% |
| Specificity | 73% | Specificity | 69% |
| Accuracy | 88% | Accuracy | 84% |
| LR+ | 3.7 | LR+ | 3.0 |
| LR− | 0 | LR− | 0.07 |
| PPV | 0.82 | PPV | 0.81 |
| NPV | 1 | NPV | 0.90 |

TABLE 2

Diagnostic agreement according to AASM scoring criteria.

| According to 1 or more technicians | | According to mean AHI-p | |
|---|---|---|---|
| Sensitivity | 100% | Sensitivity | 96% |
| Specificity | 70% | Specificity | 64% |
| Accuracy | 86% | Accuracy | 81% |
| LR+ | 3.3 | LR+ | 2.7 |
| LR− | 0 | LR− | 0.06 |
| PPV | 0.79 | PPV | 0.75 |
| NPV | 1 | NPV | 0.94 |

When employing PSG for diagnosis of SA, the AHI is calculated by dividing the number of apneas and hypopneas by the total sleep time. However, since the above-described system is, at least in some embodiments, contemplated for use in a home setting where sleep onset is not as readily identifiable as in a sleep laboratory setting, further investigation compared the AHI-a values calculated with time-in-bed as the denominator, to AHI-p values with total sleep time as the denominator, using TV50 criteria. Validity measures revealed improvement over AHI-p based on recording time, with an overall accuracy up to 90%, as shown in Table 3, below.

TABLE 3

Diagnostic agreement between AHI-a based on time-in-bed and AHI-p based on total sleep time using TV50.

| According to 1 or more technicians | | According to mean AHI-p | |
|---|---|---|---|
| Sensitivity | 97% | Sensitivity | 93% |
| Specificity | 79% | Specificity | 72% |
| Accuracy | 90% | Accuracy | 85% |
| LR+ | 4.6 | LR+ | 3.3 |
| LR− | 0.04 | LR− | 0.09 |
| PPV | 0.88 | PPV | 0.84 |
| NPV | 0.94 | NPV | 0.88 |

As can be seen from FIG. 18, the high sensitivity of the proposed method can be attributed to the slight but systematic over scoring of cases in the lower range (AHI<15). As will be appreciated by the skilled artisan, it is generally clinically safer to over-score than to under-score border line cases in order to avoid missing diagnosis of patients who may need treatment. Of interest, the false positive cases were close to the cut-off AHI point of 10. In one embodiment, this consideration can be addressed by defining a zone of uncertainly between the AHI-a of 10 to 18 where false positives lie. Treatment of SA is ordinarily prescribed for the presence of an SA syndrome based on an AHI and the symptoms of SA determined by a clinical evaluation. Therefore, as would be the case for a borderline AHI-p, the clinical significance of an AHI-a in this zone of uncertainty for a given patient would require a clinical evaluation to assess for symptoms of a sleep disordered breath syndrome. In the presence of such symptoms, a trial of SA therapy would be justified, but in the absence of such symptoms, treatment of the borderline AHI-a would not be mandated. The tendency to over score the AHI from breath sound analysis compared to AHI-p in the lower range would thus not compromise the ability to discard negative cases as revealed by the negative predictive value (NPV) of 100% and negative likelihood ratio (LR−) of zero (i.e. when compared to one or more technicians). These data indicate that an AHI-a<10 reliably rules out the presence of SA. Such reliability in ruling out SA is an important feature of a portable sleep apnea monitoring device since it would obviate the need to perform costly PSG and prescribe unnecessary interventions to subjects with a low AHI who do not need them.

As demonstrated by the above results, significant agreement was observed between the AHI assessed by acoustic analysis of breath sounds using the above-described methods and devices, and that determined simultaneously during full in-laboratory PSG. As noted above, overall accuracy for diagnosis of SA reached 90% with 94% correlation across the spectrum of AHIs, with 98% of AHI-a falling within Bland Altman limits of agreement with AHI-p.

The above-described methods and devices thus provide a reliable and accurate approach to SA identification, characterization and/or diagnostics, while providing for a readily accessible solution for home use via the provision of a less invasive and more user friendly apparatus. Namely, unlike PSG, which generally requires specialized installation, care and operation of the 12 or more acquisition channels, the above-described system and methods can provide comparable results, in some embodiments, using as little as a single channel acquired by way of a breath-sensitive transducer positioned in a nose and mouth area of the subject.

Furthermore, while PSG generally seeks to calculate the AHI by dividing the number of apneas and hypopneas by total sleep time, which generally requires the presence of a trained technician to apply multiple electrodes to record electroencephalographic, electo-oculographic and electro-myographic signals to determine the presence, and quantify the amount and type of sleep, the above-described devices and methods dispense of such requirements while still allowing for accurate determination of the AHI based on total recording time. This again facilitates home use and increases portability of the herein-described embodiments. Regardless, the herein-described methods and devices may further incorporate a calibration factor whereby a total sleep time could be estimated as a function of a total recording time to further increase AHI accuracy. These and other such considerations will be apparent to the person of ordinary skill in the art and are thus considered to fall within the scope of the present disclosure.

As will be appreciated by the skilled artisan, these results confirm the validity of the above proposed approach, which can not only be used for diagnosing sleep apnea, but also its severity in automatically outputting an AHI (step 610), and this, in some embodiments, from the processing recorded breath sounds only.

Furthermore, the above-described example may accommodate natural variations in breath sounds, which may include, but are not limited to snoring, regular breathing and variations in acoustic amplitude levels. Not only does this flexibility allow for greater versatility in achieving usable results, it may also allow candidates suffering from different types of disorders to be diagnosed. For example, as discussed above, methods relying solely on snoring sounds do not accommodate candidates whose conditions are not necessarily manifested through snoring, such as candidates suffering from CSA for whom snoring does not necessarily occur. Comparatively, embodiments described herein may allow for a detection of sleep apnea in candidates suffering from CSA or OSA alike.

While the present disclosure describes various exemplary embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A computer-implemented method, automatically implemented by one or more processors of a computing system, for detecting apneas and hypopneas from a digitized breath sound recording acquired from a candidate suspected of sleep apnea, the method comprising:
scanning by at least one processor an amplitude profile of said digitized breath sound recording to identify a prospect event segment;

evaluating by at least one processor characteristics of said prospect event segment for consistency with one or more preset apnea-specific criteria;

classifying by at least one processor said prospect event segment as representative of an apnea upon it satisfying each of said one or more apnea-specific criteria;

evaluating by at least one processor the characteristics of said prospect event for consistency with one or more preset hypopnea-specific criteria distinct from said apnea-specific criteria;

classifying by at least one processor said prospect event segment as representative of a hypopnea upon it satisfying each of said one or more hypopnea-specific criteria; and outputting indication of a candidate's condition as a function of each said classified apnea and hypopnea;

wherein said prospect event is characterized by a falling edge and a rising edge temporally separated by a low-amplitude segment;

wherein said one or more apnea-specific criteria comprise a minimum apnea event amplitude depth threshold; and wherein said one or more hypopnea-specific criteria comprise
a distinct minimum hypopnea event amplitude depth threshold shallower than said minimum apnea event amplitude depth threshold, and wherein said distinct hypopnea event amplitude depth threshold comprises both a minimum pre-apneic depth threshold and a distinct post-apneic depth threshold.

2. The method of claim 1, the characteristics of said prospect event being evaluated for consistency with said one or more preset hypopnea-specific criteria only upon said characteristics failing to satisfy at least one of said one or more apnea-specific criteria.

3. The method of claim 1, said scanning step comprising scanning said amplitude profile to identify multiple prospect event segments, the method further comprising sequentially repeating steps subsequent to said scanning step for each of said identified prospect event segments.

4. The method of claim 1, further comprising increasing an apnea/hypopnea count for each said classified apnea and hypopnea, wherein said outputting comprises outputting a severity index representative of said candidate's condition as a function of said count.

5. The method of claim 1, said pre-apneic depth threshold being shallower than said post-apneic depth threshold.

6. The method of claim 1, said scanning step comprising scanning said amplitude profile for segments satisfying a minimum prospect event depth threshold, said minimum prospect event depth threshold at least as shallow as said minimum hypopnea event amplitude depth threshold.

7. The method of claim 1, said one or more hypopnea-specific criteria further comprising a minimum decreasing amplitude gradient for said falling edge.

8. The method of claim 1, further comprising defining said amplitude profile as a breath-to-breath amplitude profile over time.

9. The method of claim 1, further comprising extracting breath sounds associated with expiration, and defining said amplitude profile solely as a function of said extracted expiration breath sounds.

10. The method of claim 1, further comprising recording said breath sounds via a microphone embedded within a face mask to be worn by said candidate during sleep, the microphone disposed at a distance from a nose and mouth area of the candidate's face to be exposed to and thereby acquire oral and nasal expiratory airflow sounds.

11. The method of claim 1, wherein said outputting comprises outputting said indication via a user interface.

12. A non-transitory computer-readable medium comprising statements and instructions stored thereon for implementation by one or more processors of a computing system to detect apneas and hypopneas from a digitized breath sound recording acquired from a candidate suspected of sleep apnea that cause the computer system to perform the following operations:

scan by at least one processor an amplitude profile of said digitized breath sound recording to identify a prospect event segment;

evaluate by at least one processor characteristics of said prospect event segment for consistency with one or more preset apnea-specific criteria;

classify by at least one processor said prospect event segment as representative of an apnea upon it satisfying each of said one or more apnea-specific criteria;

evaluate by at least one processor the characteristics of said prospect event for consistency with one or more preset hypopnea-specific criteria distinct from said apnea-specific criteria;

classify by at least one processor said prospect event segment as representative of a hypopnea upon it satisfying each of said one or more hypopnea-specific criteria; and output indication of a candidate's condition as a function of each said classified apnea and hypopnea;

wherein said prospect event is characterized by a falling edge and a rising edge temporally separated by a low-amplitude segment;

wherein said one or more apnea-specific criteria comprise a minimum apnea event amplitude depth threshold; and wherein said one or more hypopnea-specific criteria comprise
a distinct minimum hypopnea event amplitude depth threshold shallower than said minimum apnea amplitude depth threshold, and wherein said distinct hypopnea event amplitude depth threshold comprises both a minimum pre-apneic depth threshold and a distinct post-apneic depth threshold.

13. A system for detecting apneas and hypopneas from a digitized breath sound recording acquired from a candidate suspected of sleep apnea, the system comprising:

one or more processors;

memory storing instructions, the instructions comprising instructions that, when executed by the one or more processors, cause the processors to:

scan by at least one processor an amplitude profile of said digitized breath sound recording to identify a prospect event segment;

evaluate by at least one processor characteristics of said prospect event segment for consistency with one or more preset apnea-specific criteria;

classify by at least one processor said prospect event segment as representative of an apnea upon it satisfying each of said one or more apnea-specific criteria;

evaluate by at least one processor the characteristics of said prospect event for consistency with one or more preset hypopnea-specific criteria distinct from said apnea-specific criteria;

classify by at least one processor said prospect event segment as representative of a hypopnea upon it satisfying each of said one or more hypopnea-specific criteria; and output indication of a candidate's condition as a function of each said classified apnea and hypopnea,
wherein said prospect event is characterized by a falling edge and a rising edge temporally separated by a low-amplitude segment;
wherein said one or more apnea-specific criteria comprise a minimum apnea event amplitude depth threshold; and
wherein said one or more hypopnea-specific criteria comprise
a distinct minimum hypopnea event amplitude depth threshold shallower than said minimum apnea amplitude depth threshold, and wherein said distinct hypopnea event amplitude depth threshold comprises both a minimum pre-apneic depth threshold and a distinct post-apneic depth threshold.

14. The system of claim 13, further comprising a face mask having a microphone mounted thereon and reproducibly disposable, upon the candidate wearing the mask, at a distance above a nose and mouth area of the candidate so to intercept and capture expiratory airflow sounds emanating therefrom to be digitized for processing.

15. The system of claim 14, said mask further comprising a removable data storage medium operatively coupled to said microphone for storing recorded breath sounds thereon prior to processing.

16. The non-transitory computer-readable medium of claim 12, further comprising statements and instructions that cause the processors to increase an apnea/hypopnea count for each said classified apnea and hypopnea, and wherein said output indication comprises a severity index representative of said candidate's condition and output as a function of said count.

17. The non-transitory computer-readable medium of claim 12, said pre-apneic depth threshold being shallower than said post-apneic depth threshold.

18. The non-transitory computer-readable medium of claim 12, said one or more hypopnea-specific criteria further comprising a minimum decreasing amplitude gradient for said falling edge.

19. The system of claim 14, wherein said memory further comprises statements and instructions to increase an apnea/hypopnea count for each said classified apnea and hypopnea, and wherein said output indication comprises a severity index representative of said candidate's condition and output as a function of said count.

20. A computer-implemented method, automatically implemented by one or more processors of a computing system, for detecting apneas and hypopneas from a digitized breath sound recording acquired from a candidate suspected of sleep apnea, the method comprising:
scanning by at least one processor an amplitude profile of said digitized breath sound recording to identify a prospect event segment;
evaluating by at least one processor characteristics of said prospect event segment for consistency with one or more preset apnea-specific criteria;
classifying by at least one processor said prospect event segment as representative of an apnea upon it satisfying each of said one or more apnea-specific criteria;
evaluating by at least one processor the characteristics of said prospect event for consistency with one or more preset hypopnea-specific criteria distinct from said apnea-specific criteria;
classifying by at least one processor said prospect event segment as representative of a hypopnea upon it satisfying each of said one or more hypopnea-specific criteria; and
outputting indication of a candidate's condition as a function of each said classified apnea and hypopnea;
wherein said prospect event is characterized by a falling edge and a rising edge temporally separated by a low-amplitude segment;
wherein said one or more apnea-specific criteria comprise a minimum apnea event amplitude depth threshold;
wherein said one or more hypopnea-specific criteria comprise a distinct minimum hypopnea event amplitude depth threshold shallower than said minimum apnea event amplitude depth threshold; and
wherein said scanning step comprises scanning said amplitude profile for segments satisfying a minimum prospect event depth threshold, said minimum prospect event depth threshold at least as shallow as said minimum hypopnea event amplitude depth threshold.

21. A system for detecting apneas and hypopneas from a digitized breath sound recording acquired from a candidate suspected of sleep apnea, the system comprising:
one or more processors;
memory storing instructions, the instructions comprising instructions that, when executed by the one or more processors, cause the processors to:
scan by at least one processor an amplitude profile of said digitized breath sound recording to identify a prospect event segment;
evaluate by at least one processor characteristics of said prospect event segment for consistency with one or more preset apnea-specific criteria;
classify by at least one processor said prospect event segment as representative of an apnea upon it satisfying each of said one or more apnea-specific criteria;
evaluate by at least one processor the characteristics of said prospect event for consistency with one or more preset hypopnea-specific criteria distinct from said apnea-specific criteria;
classify by at least one processor said prospect event segment as representative of a hypopnea upon it satisfying each of said one or more hypopnea-specific criteria; and
output indication of a candidate's condition as a function of each said classified apnea and hypopnea;
wherein said prospect event is characterized by a falling edge and a rising edge temporally separated by a low-amplitude segment;
wherein said one or more apnea-specific criteria comprise a minimum apnea event amplitude depth threshold;
wherein said one or more hypopnea-specific criteria comprise a distinct minimum hypopnea event amplitude depth threshold shallower than said minimum apnea amplitude depth threshold; and
wherein said scanning step comprises scanning said amplitude profile for segments satisfying a minimum prospect event depth threshold, said minimum prospect event depth threshold at least as shallow as said minimum hypopnea event amplitude depth threshold.

22. A non-transitory computer-readable medium comprising statements and instructions stored thereon for implementation by one or more processors of a computing system to detect apneas and hypopneas from a digitized breath sound recording acquired from a candidate suspected of sleep apnea that cause the computer system to perform the following operations:
scan by at least one processor an amplitude profile of said digitized breath sound recording to identify a prospect event segment;

evaluate by at least one processor characteristics of said prospect event segment for consistency with one or more preset apnea-specific criteria;

classify by at least one processor said prospect event segment as representative of an apnea upon it satisfying each of said one or more apnea-specific criteria;

evaluate by at least one processor the characteristics of said prospect event for consistency with one or more preset hypopnea-specific criteria distinct from said apnea-specific criteria;

classify by at least one processor said prospect event segment as representative of a hypopnea upon it satisfying each of said one or more hypopnea-specific criteria; and output indication of a candidate's condition as a function of each said classified apnea and hypopnea;

wherein said prospect event is characterized by a falling edge and a rising edge temporally separated by a low-amplitude segment;

wherein said one or more apnea-specific criteria comprise a minimum apnea event amplitude depth threshold;

wherein said one or more hypopnea-specific criteria comprise a distinct minimum hypopnea event amplitude depth threshold shallower than said minimum apnea amplitude depth threshold; and wherein said scanning step comprises scanning said amplitude profile for segments satisfying a minimum prospect event depth threshold, said minimum prospect event depth threshold at least as shallow as said minimum hypopnea event amplitude depth threshold.

\* \* \* \* \*